United States Patent [19]
Passmore et al.

[11] Patent Number: 5,976,846
[45] Date of Patent: Nov. 2, 1999

[54] METHOD FOR MULTIFRAGMENT IN VIVO CLONING AND MUTATION MAPPING

[76] Inventors: Steven E. Passmore; Donna L. Marykwas, both of 45 Eustis St., Cambridge, Mass. 02140

[21] Appl. No.: 08/584,322

[22] Filed: Jan. 13, 1996

[51] Int. Cl.$^6$ .................................................. C12N 15/00
[52] U.S. Cl. .......................... 435/172.3; 435/6; 435/91.2
[58] Field of Search ............................... 435/172.3, 91.2, 435/6

[56] References Cited

U.S. PATENT DOCUMENTS

| | | | |
|---|---|---|---|
| 4,237,224 | 12/1980 | Cohen et al. | 435/68 |
| 5,223,408 | 6/1993 | Goeddel et al. | 435/69.3 |
| 5,279,952 | 1/1994 | Wu et al. | 435/172.3 |
| 5,286,632 | 2/1994 | Jones | 435/91 |

OTHER PUBLICATIONS

Denise Muhlrad et al. (1992) "A Rapid Method for Localized Mutagenesis of Yeast Genes" Yeast 8, 79–82.

Craig Tuerk et al. (1994) "In Vitro Evolution of Functional Nucleic Acids: High–Affinity RNA Ligands of the HIV–1 rev Protein" In The Polymerase Chain Reaction, K.B. Mullis, F. Ferré, R.A. Gibbs, editors 233–243.

Eric Degryse et al. (1995) "In Vivo Cloning by Homologous Recombination in Yeast Using a Two–Plasmid–Based System" Yeast 11, 629–640.

E. Schärer and R. Iggo (1992) "Mammalian p53 can function as a transcription factor in yeast" Nucleic Acids Research 20, 1539–1545.

Sam Kunes et al. (1987) "Fine Structure Recombinational Analysis of Cloned Genes Using Yeast Transformation" Genetics 115, 73–81.

Rodney Rothstein. (1991) "Targeting, Disruption, Replacement, and Allele Rescue: Integrative DNA Transformation in Yeast" Methods in Enzymology 194, 281–301.

Peter C. Turner and Moyer, Richard W. (1992) "A PCR–Based Method for Manipulation of the Vaccina Virus Genome That Eliminates the Need for Cloning" BioTechniques 13, 764–771.

Hong Ma et al. (1987) "Plasmid construction by homologous recombination in yeast" Gene 58, 201–216.

(List continued on next page.)

*Primary Examiner*—W. Gary Jones
*Assistant Examiner*—Ethan Whisenant

[57] ABSTRACT

The subject invention relates to a method referred to as multifragment in vivo cloning (MFIVC). In the method, the polymerase chain reaction or the cleavage by restriction enzyme(s) are used to generate a series of double-stranded DNA fragments. Each fragment contains a region homologous to a portion of the fragment to which it is to be joined. These homologous regions undergo recombination in vivo following transformation into a host with efficient and precise homologous recombination (such as the yeast *S. cerevisiae*). A series is designed so that the last fragment in the series contains a region homologous to a portion of the first fragment in the series, thus forming a circular DNA molecule after recombination in vivo. A circular DNA molecule can be selected in vivo if the circular DNA molecule created contains both a suitable DNA replication origin and a suitable marker for genetic selection. A series may be designed so that the first and last fragment in the series contain telomeric sequence elements, forming a linear DNA molecule with telomeric sequence elements at its ends, after recombination in vivo. One preferred embodiment of this method includes a means for mapping a phenotypically expressed mutation within a gene. A second embodiment of this method includes a means for constructing plasmids using DNA cassettes. A third embodiment of this method includes a means of reasserting mutations in a double-stranded DNA molecule. The invention also includes kits containing reagents for conducting the method.

15 Claims, 8 Drawing Sheets

OTHER PUBLICATIONS

Douglas H. Jones and Winistorfer, Stanley C. (1992) "Recombinant Circle PCR and Recombination PCR for Site–Specific Mutagenesis Without PCR Product Purification" BioTechniques 12, 528–534.

Jonathan D. Oliner et al. (1993) "In vivo cloning of PCR products in E. coli" Nucleic Acids Research 21, 5192–5197.

Douglas H. Jones and Howard, Bruce H. (1990) "A Rapid Method for Site–Specific Mutagenesis and Directional Subcloning by Using the Polymerase Chain Reaction to Generate Recombinant Circles" BioTechiques 8, 178–183.

Douglas H. Jones and Howard, Bruce H. (1991) "A Rapid Method for Recombination and Site–Specific Mutagenesis by Placing Homologous Ends on DNA Using Polymerase Chain Reaction" BioTechniques 10, 62–66.

Willem P. C. Stemmer (1994) "Rapid evolution of a protein in vitro by DNA shuffling" Nature 370, 389–391.

Willem P. C. Stemmer (1994b) "DNA shuffling by random fragmentation and reassembly: In vitro recombination for molecular evolution" Proc. Natl. Acad. Sci. USA 91, 10747–10751.

Donna L. Marykwas and Passmore, Steven E. (1995) "Mapping by multifragment cloning in vivo" Proc. Natl. Acad. Sci USA 92, 11701–11705.

Jones et al., Nature 344: 793–794 (1990).

Jones et al., Biotechniques 16(4) : 694–701 (1994).

Ho et al., Gene 77 : 51–59 (1989).

Horton et al., Gene : 61–68 (1989).

Fisch et al., PNAS 93 : 7761–7766 (1996).

Genes

Fragments tested

Hybrid plasmids

Phenotypes

Wild-type         Wild-type         Mutant

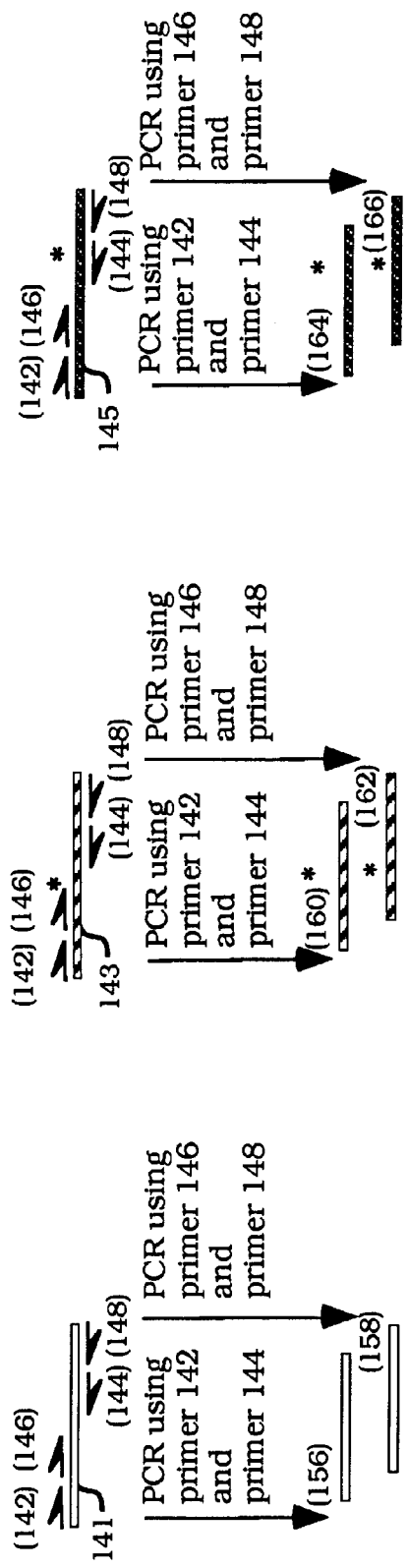

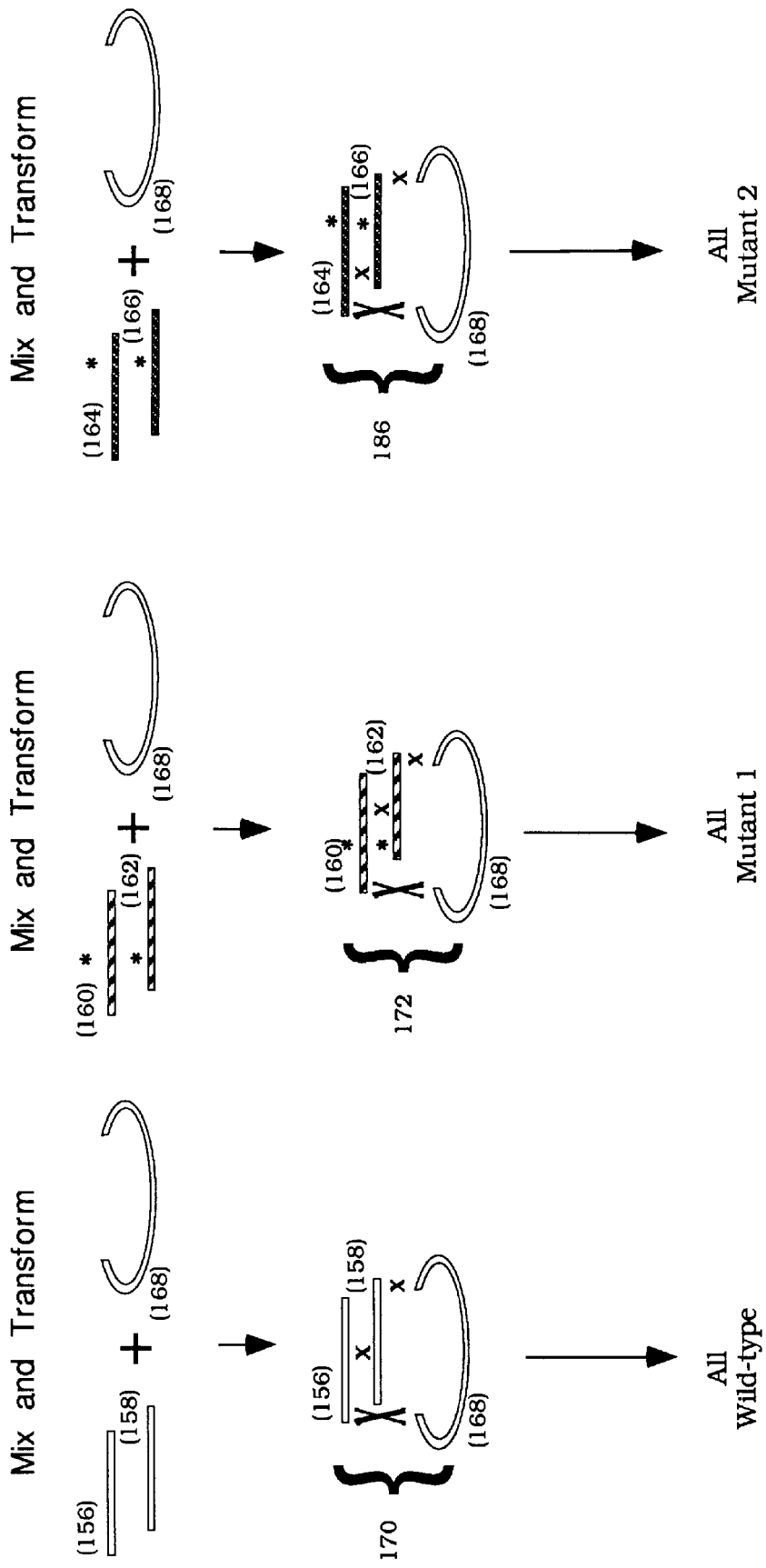

SEQUENCE LISTING (1) GENERAL INFORMATION:

(iii) NUMBER OF SEQUENCES:8

(2) INFORMATION FOR SEQ ID NO: 1:

(i) SEQUENCE CHARACTERISTICS:
          (A) LENGTH:18 base pairs
          (B) TYPE:nucleic acid
          (C) STRANDEDNESS:single
          (D) TOPOLOGY:linear (ii) MOLECULE TYPE: Other nucleic acid (Synthetic DNA)

(xi) SEQUENCE DESCRIPTION: SEQ ID NO: 1:

TCATCGGAAG AGAGTAGT                                                 18

(2) INFORMATION FOR SEQ ID NO: 2:

(i) SEQUENCE CHARACTERISTICS:
          (A) LENGTH:20 base pairs
          (B) TYPE:nucleic acid
          (C) STRANDEDNESS:single
          (D) TOPOLOGY:linear (ii) MOLECULE TYPE: Other nucleic acid (Synthetic DNA)

(xi) SEQUENCE DESCRIPTION: SEQ ID NO: 2:

GACCGACCTC ATGCTATACC                                               20

(2) INFORMATION FOR SEQ ID NO: 3:

(i) SEQUENCE CHARACTERISTICS:
          (A) LENGTH:18 base pairs
          (B) TYPE:nucleic acid
          (C) STRANDEDNESS:single
          (D) TOPOLOGY:linear (ii) MOLECULE TYPE: Other nucleic acid (Synthetic DNA)

(xi) SEQUENCE DESCRIPTION: SEQ ID NO: 3:

AGATATTCTC GAAACTCG                                                 18

(2) INFORMATION FOR SEQ ID NO: 4:

(i) SEQUENCE CHARACTERISTICS:
          (A) LENGTH:18 base pairs
          (B) TYPE:nucleic acid
          (C) STRANDEDNESS:single
          (D) TOPOLOGY:linear (ii) MOLECULE TYPE: Other nucleic acid (Synthetic DNA)

(xi) SEQUENCE DESCRIPTION: SEQ ID NO: 4:

CGATAATTTG CGGATGCT                                                 18

(2) INFORMATION FOR SEQ ID NO: 5:

(i) SEQUENCE CHARACTERISTICS:
          (A) LENGTH:18 base pairs
          (B) TYPE:nucleic acid
          (C) STRANDEDNESS:single
          (D) TOPOLOGY:linear (ii) MOLECULE TYPE: Other nucleic acid (Synthetic DNA)

(xi) SEQUENCE DESCRIPTION: SEQ ID NO: 5:

```
CTGATGAAAA CTCAGCAG                                                          18

(2) INFORMATION FOR SEQ ID NO: 6:

(i) SEQUENCE CHARACTERISTICS:
        (A) LENGTH:18 base pairs
        (B) TYPE:nucleic acid
        (C) STRANDEDNESS:single
        (D) TOPOLOGY:linear (ii) MOLECULE TYPE: Other nucleic acid (Synthetic DNA)

(xi) SEQUENCE DESCRIPTION: SEQ ID NO: 6:

CTCGAACAGG AACATCTC                                                          18

(2) INFORMATION FOR SEQ ID NO: 7:

(i) SEQUENCE CHARACTERISTICS:
        (A) LENGTH:19 base pairs
        (B) TYPE:nucleic acid
        (C) STRANDEDNESS:single
        (D) TOPOLOGY:linear (ii) MOLECULE TYPE: Other nucleic acid (Synthetic DNA)

(xi) SEQUENCE DESCRIPTION: SEQ ID NO: 7:

GCCGCCGATA TTCTGGCGT                                                         19

(2) INFORMATION FOR SEQ ID NO: 8:

(i) SEQUENCE CHARACTERISTICS:
        (A) LENGTH:16 base pairs
        (B) TYPE:nucleic acid
        (C) STRANDEDNESS:single
        (D) TOPOLOGY:linear (ii) MOLECULE TYPE: Other nucleic acid (Synthetic DNA)

(xi) SEQUENCE DESCRIPTION: SEQ ID NO: 8:

ACGTTCATCG AACAAC                                                            16
```

METHOD FOR MULTIFRAGMENT IN VIVO CLONING AND MUTATION MAPPING

BACKGROUND-FIELD OF INVENTION

The present invention is in the field of recombinant DNA technology. This invention relates to a process for assembling multiple DNA fragments in vivo, and to the molecules employed and produced through this process. Thus, the method can be used for the rapid generation of recombinant constructs and for mapping phenotypically expressed mutations.

BACKGROUND-DESCRIPTION OF PRIOR ART

Two of the fundamental tools of the field of recombinant DNA technology are the ability to recombine DNA, and the ability to localize (or map) the position of phenotypically expressed mutations.

Methods to assemble DNA fragments into plasmids that can replicate in vivo are of fundamental importance in the field of recombinant DNA technology. Such methods can be used, for example, to construct a plasmid bearing a particular gene being studied. Typically, such methodologies involve the introduction of a nucleic acid fragment into a DNA or RNA vector, the clonal amplification of the vector (and the recovery of the amplified fragment). Examples of such methodologies are provided by Cohen et al. (U.S. Pat. No. 4,237,224), and Maniatis, T. et al., Molecular Cloning (A Laboratory Manual), Cold Spring Harbor Laboratory, 1982.

The desire to increase the utility and applicability of such methods is often frustrated by the lack of (suitable) restriction enzyme sites present at desired locations and, even when suitable restriction sites are present, by the methodological complexities involved in complex 3-way and 4-way ligations (such as sequential digestions, fragment isolation, and buffer incompatibility). Hence, it would be highly desirable to develop a general, simple, and rapid method to assemble multiple DNA fragments.

The polymerase chain reaction (PCR) technique was conceived and developed by the Cetus Corporation to provide for specific amplification of discrete fragments of DNA in order to allow simplified detection and purification of nucleic acid fragments initially present in a particular sample in only picogram quantities (Salki, et al. Science 230:1350–1354, 1985). The basic method is based on the repetition of three steps, all conducted in a successive fashion under controlled temperature conditions: (1) denaturing the double-stranded template DNA; (2) annealing the single-stranded primers to the complementary single-stranded regions on the template DNA; and, (3) synthesizing additional DNA along the templates by extension of the primer DNAs with DNA polymerase after 4 to 25 cycles of these steps; as much as a 100,000-fold increase in the amount of the original DNA is observed (Oste, BioTechniques 6:162–167, 1988). Reviews of the polymerase chain reaction are provided by Mullis, K. B. Cold Spring Harbor Symp. Quant. Biol. 51:263–273 (1986); and Mullis, K. B. et al. Meth. Enzymol. 155:335–350 (1987), which are incorporated herein by reference.

More recently, the PCR technology has been used for mutagenesis of specific DNA sequences and for other directed manipulations of DNA. For instance, PCR technology has been used to engineer hybrid (chimeric) genes without the need to use restriction enzymes in order to segment the gene prior to hybrid formation. In this approach, fragments that are to form the hybrid are generated in separate polymerase chain reactions. The primers used in these separate reactions are designed so that the ends of the different products of the separate reactions contain complementary sequences. When these separately produced PCR products are mixed, denatured, and reannealed, the strands having matching sequences at their 3'-ends overlap and act as primers for each other. Extension of this overlap by DNA polymerase produces a molecule in which the original sequences are spliced together to form a hybrid gene. Thus, this method requires four primers to construct a deleted, hybrid DNA molecule. Likewise, the method requires six primers and three rounds of PCR in order to construct a chimeric molecule (Horton, et al., Gene 77:61–68, 1989).

Recently Jones (U.S. Pat. No. 5,286,632) has described a method that can be used to join two DNA molecules. In this method, the polymerase chain reaction is utilized to add double-stranded regions to both ends of an insert DNA homologous to the ends of a linear vector. These homologous ends undergo recombination with a linear vector in vivo following transformation of *Escherichia coli*. This method can be used to introduce mutations into a preexisting vector but can not be used to rearrange (recombine) preexisting mutations present on separate DNA inserts. This method can be used to join at most two DNA molecules; this is a significant disadvantage since it is often desirable to join 3 DNA molecules. This method also requires that the homologous regions which undergo recombination be located at the ends of the DNA molecules amplified by PCR, thus necessitating the design and synthesis of primers unique for each particular pair of gene and cloning vector. An additional drawback of this method is a requirement to either purify both PCR fragments after amplification or to cut the template plasmids with a restriction enzyme that recognizes a site outside of the region to be amplified prior to amplification. An additional disadvantage of the in vivo cloning procedure described in the Jones patent (U.S. Pat. No. 5,286,632) is the extreme inefficiency of the recombination events; the recombination is less than one in 10,000,000-fold as efficient as transformation of intact plasmid.

Muhlrad et al. have described a method to introduce mutations into genes cloned into plasmids that replicate in yeast. (Muhlrad, D., Hunter, R., and Parker, R. Yeast 8:79–82, 1992). This method can not be used to rearrange (recombine) preexisting mutations present on DNA fragments. This method can be used to join at most 2 DNA molecules; this is a significant disadvantage.

Oliner et al. have described another method of in vivo cloning utilizing an *E. coli* strain with enhanced in vivo recombination (Oliner, J. D., Kinzler, K. W., and Vogelstein, B. Nucleic Acids Research 21:5192–5197, 1993). Although this method has an improved transformation efficiency compared to the methods described in the Jones patent (U.S. Pat. No. 5,286,632), the transformation efficiency is still approximately 100,000-fold lower than that of intact plasmid DNA transformed into *E. coli*, and the likelihood of efficient trimolecular and higher order recombinations would be extremely low.

Willem P. C. Stemmer (Stemmer, W. (1994) Nature 370, 389–391) has described a method for in vitro homologous recombination called DNA shuffling. In this method, pools of selected mutant genes are recombined in vitro by random fragmentation and PCR reassembly. In this method, the recombined molecules had to be cloned into an appropriate vector before transformation into *E. coli* and subsequent selection and analysis. This recloning step had to be repeated for each iteration of the selection process.

An alternative method for recombinational mapping of plasmid-borne genes in yeast has been described (Kunes, S., Ma, H., Overbye, K., Fox, M. S., & Botstein, D. (1987) *Genetics* 115: 73–81). The method of Kunes et al. relies upon the incidence of loss of a plasmid-borne mutation to identify its location. This method is based on a statistical analysis and provides a genetic map distance of a mutation from the end of a DNA fragment, the position of the end being determined by the fortuitous location of a restriction enzyme recognition site. This method is based on the loss of a plasmid-borne mutation to identify its location; in the process the mutation is lost rather than subcloned. Ma et al. have presented a method for constructing plasmids in yeast by homologous recombination (Ma, H., Kunes, S. Schatz, P. J. and Botstein, D., *Gene* 58: 201–216). However, this method can not be used to rearrange (recombine) preexisting mutations present on DNA fragments. This method can be used to join at most 2 DNA molecules; this is a significant disadvantage.

Degryse et al. in vivo cloning by homologous recombination in yeast using a two-plasmid-based system Yeast 11,629–640. This method can be used to join at most 2 DNA molecules; this is a significant disadvantage. An additional drawback of this method is the requirement that one must first construct, using conventional methods, the two plasmids used in the two-plasmid-based system.

OBJECTS AND ADVANTAGES

We describe a method to join multiple DNA fragments. This method utilizes recombination between sequence elements present at the end(s) of a series of DNA fragments to specify the junctions and uses recombination enzymes present in vivo to accomplish the joining. This method is superior to previous methods because it does not require the use of any specific DNA restriction or modification enzymes in vitro, other than those used in the PCR process.

This method is superior to previous methods because it can be used to join 3 or more DNA fragments precisely in a single procedure. This is an essential step of a process we describe in detail termed cassette-based cloning, that can be used to construct plasmids rapidly from premade parts that can be combined in a multitude of combinations.

This method is superior to previous methods because it can be used to recombine mutations present on separate DNA inserts into a single new insert, carried on a cloning vector. This is an essential step of a process we describe in detail termed directed-evolution, that can be used to incrementally modify the function (activity, affinity, thermal stability or some related property) of a protein (or catalytic RNA or DNA).

This method is superior to previous methods because it can be used to phenotypically map mutations to a particular physical DNA fragment, and in the same process subclone the phenotypic mutation away from any other mutations that might be present.

This method is superior to previous methods because it can be used to construct vectors that stably transform yeast and that contain only endogenous yeast sequences. Plasmids constructed in yeast and lacking any foreign (non-yeast) DNA might prove desirable in some circumstances where more traditional, foreign DNA-containing plasmids would be unacceptable because of regulatory prohibitions and/or social stigmas associated with the use of recombinant DNA.

Other objects and advantages will become apparent from the specifications and drawings.

FIGURES

FIG. 1: A multifragment cloning method based on homology introduced at one end of each fragment in a series.

FIG. 2: A multifragment cloning method based on homology introduced at both ends of each fragment in a series.

FIG. 3: A method of recombinational mapping of mutations.

FIG. 4: Recombinational mapping of mutations, a specific example.

FIG. 5: Cassette-based cloning methods.

FIG. 6: Directed-evolution based on multifragment cloning.

REFERENCE NUMERALS IN DRAWINGS

FIG. 1. A Multifragment Cloning Method Based on Homology Introduced at One End of Each Fragment in a Series

10 primer homologous to one end of the top strand of a yeast marker gene (11).

11 A DNA fragment that is a source of a yeast marker gene.

12 A primer with a 3' end complementary to the end of the top strand of the yeast marker gene (11), distal to the primer (10), and with a 5' end complementary to a primer (13).

13 A primer homologous to one end of the top strand of a yeast replication sequence element (14).

14 A DNA fragment that is a source of a yeast replication sequence element.

15 A primer with a 3' end complementary to the end of the top strand of the yeast replication sequence element (14), distal to the primer (13), and with a 5' end complementary to a primer (16).

16 A primer homologous to one end of the top strand of a gene to be cloned (17).

17 A DNA fragment that is a source of a gene to be cloned.

18 A primer with a 3' end complementary to the end of the top strand of the gene to be cloned (17), distal to the primer (16), and with a 5' end complementary to the primer (10).

20 A DNA fragment [generated using the PCR process] that bears the yeast selectable marker and an end homologous to a fragment (22) that bears the yeast replication sequence element, introduced as a result of the PCR process using the primer (12).

22 A DNA fragment [generated using the PCR process] that bears the yeast replication sequence element and an end homologous to a fragment (24) that bears the gene to be cloned, introduced as a result of the PCR process using the primer (15).

24 A DNA fragment [generated using the PCR process] that bears the gene to be cloned and an end homologous to the fragment (20) that bears the yeast selectable marker, introduced as a result of the PCR process using the primer (18).

26 An in vivo recombination intermediate between the overlapping DNA fragments (20), (22), and (24).

28 A recombinant plasmid, a product resulting from the in vivo recombination process, that bears the yeast selectable marker (11), the yeast replication sequence element (14), and the gene to be cloned (17).

FIG. 2 A Multifragment Cloning Method Based on Homology Introduced at Both Ends of Each Fragment in a Series

30 A primer with a 3' end homologous to one end of the top strand of the yeast marker gene (11) and with a 5' end complementary to the 5' end of a primer (40).

32 A primer with a 3' end complementary to the end of the top strand of the yeast marker gene (11), distal to the primer (30), and with a 5' end complementary to the 5' end of a primer (34).

34 A primer with a 3' end homologous to one end of the top strand of the yeast replication sequence element (14) and with a 5' end complementary to the 5' end of the primer (32).

36 A primer with a 3' end complementary to the end of the top strand of the yeast replication sequence element (14), distal to the primer (34), and with a 5' end complementary to the 5' end of a primer (38).

38 A primer with a 3' end homologous to one end of the top strand of the gene to be cloned (17) and with a 5' end complementary to the 5' end of the primer (36).

40 A primer with a 3' end complementary to the end of the top strand of the gene to be cloned (17), distal to the primer (38), and with a 5' end complementary to the 5' end of the primer (30).

42 A DNA fragment [generated using the PCR process] that bears the yeast selectable marker and a 5' end (a synthetic recombination target) derived from the 5' end of the primer (30) as well as a 3' end (a second synthetic recombination target) derived from the 5' end of the primer (32).

44 A DNA fragment [generated using the PCR process] that bears the yeast replication sequence element and a 5' end (a synthetic recombination target) derived from the 5' end of the primer (34) as well as a 3' end (a second synthetic recombination target) derived from the 5' end of the primer (36).

46 A DNA fragment [generated using the PCR process] that bears the gene to be cloned and a 5' end (a synthetic recombination target) derived from the 5' end of the primer (38) as well as a 3' end (a second synthetic recombination target) derived from the 5' end of the primer (40).

48 An in vivo recombination intermediate between the overlapping DNA fragments (42), (44), and (46).

50 A recombinant plasmid, a product resulting from the in vivo recombination process, that bears the yeast selectable marker (11), the yeast replication sequence element (14), and the gene to be cloned (17). The yeast selectable marker (11) and the yeast replication sequence element (14) are linked via the recombination targets found at the 3' end of the DNA fragment (42) and the 5' end of the DNA fragment (44). The yeast replication sequence element (14) and the gene to be cloned (17) are linked via the recombination targets found at the 3' end of the DNA fragment (44) and the 5' end of the DNA fragment (46). The gene to be cloned (17) and the yeast selectable marker (11) are linked via the recombination targets found at the 3' end of the DNA fragment (46) and the 5' end of the DNA fragment (42).

FIG. 3 A method of Recombinational Mapping of Mutations

52 A source of wild-type DNA of a gene of interest.

54 A source of mutant DNA of the gene of interest.

56 A primer homologous to the 5' end of the top strand of the gene of interest, either the wild-type (52) or the mutant (54) allele.

58 A primer complementary to an internal region of the top strand of the gene of interest, either the wild-type (52) or the mutant (54) allele.

60 A fragment [that can be derived by PCR] from the wild-type gene (52) [that can be amplified by PCR using the primers (56) and (58)] that extends from the sequence to which the primer (56) is homologous to the sequence to which the primer (58) is complementary.

62 A primer homologous to an internal region of the top strand of either the wild-type (52) or the mutant (54) gene of interest and located 5' to the sequence to which the primer (58) is complementary.

64 A primer complementary to the 3' end of the top strand of the gene of interest, either the wild-type (52) or the mutant (54) allele.

66 A fragment [that can be derived by PCR] from the wild-type gene (52) [that can be amplified by PCR using the primers (62) and (64)] that extends from the sequence to which the primer (62) is homologous to the sequence to which the primer (64) is complementary.

68 A fragment [that can be derived by PCR] from the mutant gene (54) [that can be amplified by PCR using the primers (56) and (58)] that extends from the sequence to which the primer (56) is homologous to the sequence to which the primer (58) is complementary.

70 A fragment [that can be derived by PCR] from the mutant gene (54) [that can be amplified by PCR using the primers (62) and (64)] that extends from the sequence to which the primer (62) is homologous to the sequence to which the primer (64) is complementary.

72 A linear acceptor plasmid into which the DNA fragments (60 or 68) and (66 or 70) can be recombined in vivo.

FIG. 4 Recombinational Mapping of Mutations, a Specific Example.

80 A DNA fragment that includes a wild-type copy of the fliG gene, fused between GAL4 and ADH1 DNA on a yeast expression vector, and that encodes a GAL4 DNA-binding domain-FliG fusion protein.

82 A DNA fragment that includes a mutant allele of the fliG gene, fused between GAL4 and ADH1 DNA on a yeast expression vector, and that encodes a GAL4 DNA-binding domain-FliG fusion protein.

84 A DNA oligonucleotide primer (called "I") that is homologous to the top strand of a region of the DNA that encodes the GAL4 DNA-binding domain [contained within both the wild-type (80) and the mutant (82) GAL4-fliG gene fusions].

86 A DNA oligonucleotide primer (called "A") that is homologous to the top strand of a region of the DNA that encodes FliG [contained within both the wild-type (80) and the mutant (82) GAL4-fliG gene fusions] located 3' of the primer (84) and 5' of a primer (88).

88 A DNA oligonucleotide primer (called "C") that is homologous to the top strand of a region of the DNA that encodes FliG [contained within both the wild-type (80) and the mutant (82) GAL4-fliG gene fusions] located 3' of the primer (86) and 5' of the ADH1 terminator (a DNA sequence element that signals the termination of transcription).

90 A DNA oligonucleotide primer (called "B") that is complementary to a region of the top strand of the DNA that encodes FliG [contained within both the wild-type (80) and the mutant (82) GAL4-fliG gene fusions] located between the primers (86) and (88).

92 A DNA oligonucleotide primer (called "D") that is complementary to a region of the top strand of the DNA that encodes FliG [contained within both the wild-type (80) and the mutant (82) GAL4-fliG gene fusions] located between the primer (88) and the ADH1 terminator.

94 A DNA oligonucleotide primer (called "T") that is complementary to a region of the top strand of the ADH1 terminator [contained within both the wild-type (80) and the mutant (82) GAL4-fliG gene fusions].

96 A DNA fragment amplified from the wild-type fliG (80) template using PCR and the primers (84) and (90).

98 A DNA fragment amplified from the mutant fliG (82) template using PCR and the primers (86) and (94).

100 A DNA fragment amplified from the mutant fliG (82) template using PCR and the primers (84) and (90).

102 A DNA fragment amplified from the wild-type fliG (80) template using PCR and the primers (86) and (94).

104 A DNA fragment amplified from the wild-type fliG (80) template using PCR and the primers (84) and (92).

106 A DNA fragment amplified from the mutant fliG (82) template using PCR and the primers (88) and (94).

108 A DNA fragment amplified from the wild-type fliG (80) template using PCR and the primers (84) and (92).

110 A DNA fragment amplified from the wild-type fliG (80) template using PCR and the primers (88) and (94).

112 A linear receptor plasmid that has DNA homology at one end to GAL4 DNA [the part of GAL4 present on DNA fragments (96), (100), (104), and (108)] and at the other end to ADH1 DNA [the part of ADH1 present on DNA fragments (98), (102), (106), and (110)]. The portion of GAL4 present on the linear plasmid (112), when recombined with the overlapping GAL4 DNA on either fragment (96), (100), (104), or (108), is sufficient to reconstruct the GAL4 DNA-binding domain coding sequence. Similarly, the portion of ADH1 present on the linear plasmid (112), when recombined with the overlapping ADH1 DNA on fragment (98), (102), (106), or (110), is sufficient to reconstruct a complete ADH1 terminator element.

FIG. 5 Cassette-Based Cloning Methods

114 A primer homologous to a recombination element at the 5' end of a "marker cassette."

116 A primer complementary to a second unique recombination element at the 3' end of the "marker cassette."

118 A primer with a 3' end homologous to an oligo target sequence at the 5' end of a "replication cassette" and with a 5' end homologous to the recombination element at the 3' end of the "marker cassette."

120 A primer complementary to a third unique recombination element at the 3' end of the "replication cassette."

122 A primer with a 3' end homologous to the 5' end of a gene to be cloned and with a 5' end homologous to the recombination element at the 3' end of the "replication cassette."

124 A primer with a 3' end complementary to the 3' end of the gene to be cloned and with a 5' end complementary to the recombination element at the 5' end of the "marker cassette."

126 A source of a marker cassette, for example, a plasmid or a linear DNA fragment, that contains a yeast selectable marker bounded by the 5' marker recombination element and the 3' marker recombination element. By using different yeast genes separately cloned into the same or similar vectors, interchangeable cassettes of different selectable markers can be generated.

128 A source of a replication cassette, for example, a plasmid or a linear DNA fragment, that contains a yeast replication element bounded by the 5' oligo target sequence and the 3' replication recombination element. By using different yeast replication elements separately cloned into the same or similar vectors, interchangeable cassettes of different recombination elements can be generated.

130 A source of the gene to be cloned.

132 A linear fragment that contains the yeast selectable marker bounded by the 5' marker recombination element and the 3' marker recombination element. This fragment is generated by PCR using the marker cassette source (126) as template and the primers (114) and (116).

134 A linear fragment that contains the yeast replication element bounded by the 5' replication recombination element (homologous to the 3' marker recombination element) and by the 3' replication recombination element. This fragment is generated by PCR using the replication cassette source (128) as template and the primers (118) and (120).

136 A linear fragment that contains the gene to be cloned bounded by a 5' recombination element (homologous to the 3' replication recombination element) and a 3' recombination element (homologous to the 5' marker recombination element). This fragment is generated by PCR using the gene source (130) as template and the primers (122) and (124).

138 An in vivo recombination intermediate between the overlapping DNA fragments (132), (134), and (136).

140 A recombinant plasmid, a product of homologous recombination, generated in vivo.

FIG. 6 Directed-Evolution Based on Multifragment Cloning

141 A wild-type evolution cassette; a source of a wild-type gene to be evolved, having at its 3' end a region homologous to one end of a gapped vector (168) and at its 5' end a region homologous to the other end of a gapped vector (168).

142 A primer homologous to the 5' end of a DNA (evolution cassette) to be evolved and also homologous to one end of a linearized gapped vector (168).

143 A mutant evolution cassette; a source of a mutant gene bearing mutation 1 (isolated in a primary selection for improved gene function; one of many such mutations that are present in a pool of selected genes).

144 A primer complementary to a region near the 3' end of the DNA (evolution cassette) to be evolved, but not within a terminal region of homology to a linearized gapped vector (168).

145 A second mutant evolution cassette; a source of a mutant gene bearing mutation 2 (isolated in a primary selection for improved gene function; one of many such mutations that are present in a pool of selected genes).

146 A primer homologous to a region near the 5' end of a DNA (evolution cassette) to be evolved, but not within a terminal region of homology to a linearized gapped vector (168).

148 A primer complementary to the 3' end of a DNA (evolution cassette) to be evolved, located within a region that is homologous to the other end of a linearized gapped vector (168).

156 A DNA fragment amplified by PCR from the wild-type DNA source (141) using the primers (142) and (144).

158 A DNA fragment amplified by PCR from the wild-type DNA source (141) using the primers (146) and (148).

160 A DNA fragment amplified by PCR from the mutation 1 DNA source (143) using the primers (142) and (144).

162 A DNA fragment amplified by PCR from the mutation 1 DNA source (143) using the primers (146) and (148).

164 A DNA fragment amplified by PCR from the mutation 2 DNA source (145) using the primers (142) and (144).

166 A DNA fragment amplified by PCR from the mutation 2 DNA source (145) using the primers (146) and (148).

168 A linearized and gapped acceptor plasmid with a DNA replication origin and a marker that can be selected for in yeast.

170 A recombination intermediate between the gapped acceptor plasmid (168), the wild-type fragment (156), and the overlapping wild-type fragment (158). Recombination in vivo regenerates the wild-type gene, on a vector.

172 A recombination intermediate between the gapped acceptor plasmid (168), the DNA fragment (160) containing mutation 1, and the DNA fragment (162) also containing mutation 1. Recombination in vivo regenerates mutation 1, on a vector.

174 A recombination intermediate between the gapped acceptor plasmid (168), the DNA fragment (160) containing mutation 1, and the DNA fragment (166) containing mutation 2, regenerating a mutation 1-bearing vector.

176 A recombination intermediate between the gapped acceptor plasmid (168), the DNA fragment (160) containing mutation 1, and the DNA fragment (166) containing mutation 2, regenerating a mutation 1-mutation 2 double-mutant-bearing vector.

178 A recombination intermediate between the gapped acceptor plasmid (168), the DNA fragment (160) containing mutation 1, and the DNA fragment (166) containing mutation 2, regenerating a mutation 2-bearing vector.

180 A recombination intermediate between the gapped acceptor plasmid (168), the DNA fragment (164) containing mutation 2, and the DNA fragment (162) containing mutation 1, regenerating a mutation 1-bearing vector.

182 A recombination intermediate between the gapped acceptor plasmid (168), the DNA fragment (164) containing mutation 2, and the DNA fragment (162) containing mutation 1, regenerating a wild-type-bearing vector.

184 A recombination intermediate between the gapped acceptor plasmid (168), the DNA fragment (164) containing mutation 2, and the DNA fragment (162) containing mutation 1, regenerating a mutation 2-bearing vector.

186 A recombination intermediate between the gapped acceptor plasmid (168), the DNA fragment (164) containing mutation 2, and the DNA fragment (166) also containing mutation 2, regenerating a mutation 2-bearing vector.

DETAILED DESCRIPTION OF THE INVENTION

Description-FIGS. 1 to 6

Figure 1:
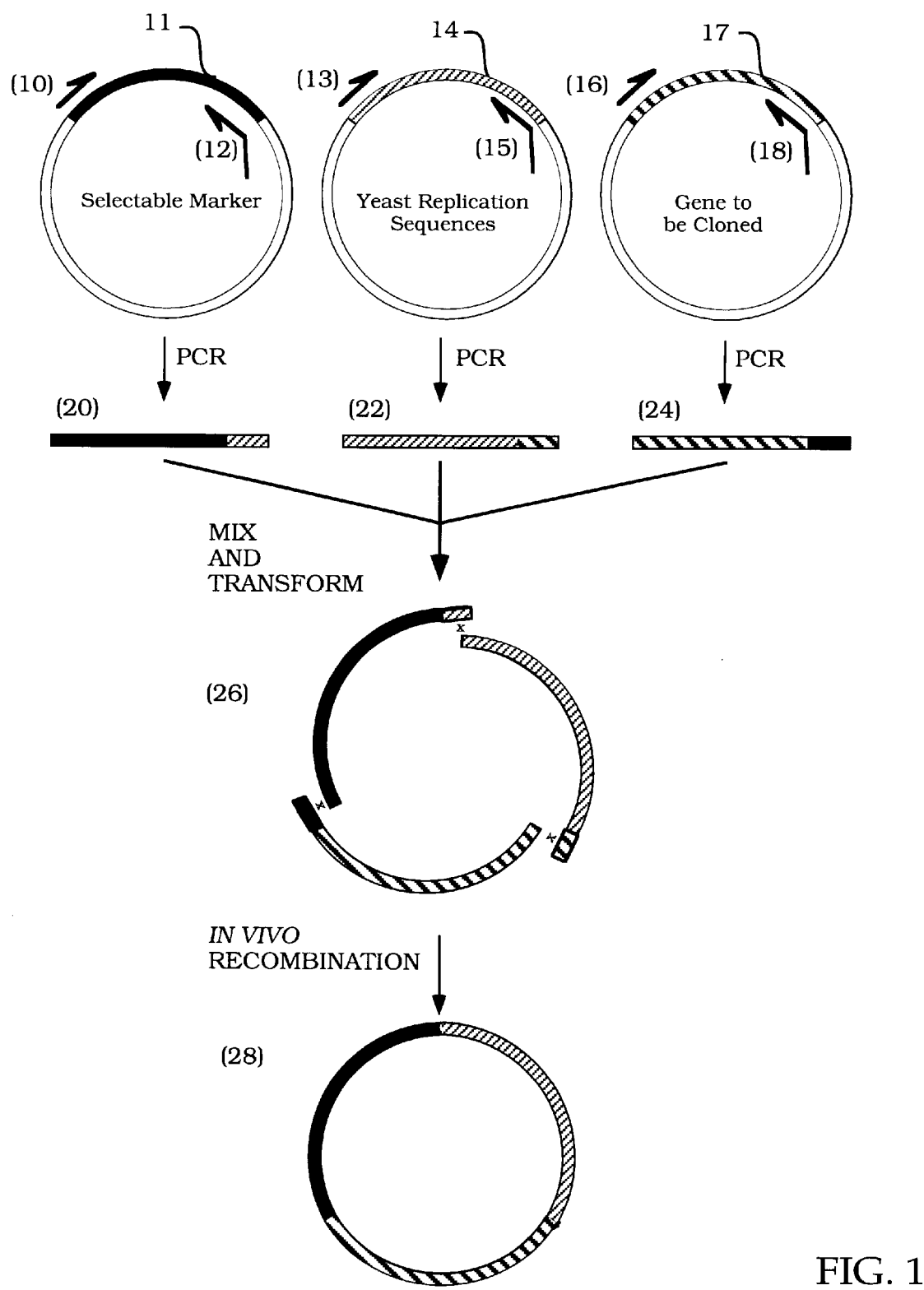

FIG. 1 A Multifragment Cloning Method Based on Homology Introduced at One End of Each Fragment in a Series A method of cloning DNA is described. This method is based on the ability to create a series of overlapping DNA fragments by introducing at one end of each DNA fragment a sequence element homologous to the next DNA fragment in the series (see FIG. 1).

This method can be used to construct vectors that stably transform yeast and that contain only endogenous yeast sequences.

This method requires a host with an efficient and highly accurate recombination system. We have found that the yeast *Saccharomyces cerevisiae* serves as a suitable transformation host for this method. We have tested many strains of *S. cerevisiae* and all have served as suitable hosts. We have tested other possible transformation hosts, including several strains of *E. coli*, but so far we have not identified any other hosts suitable for use in this method.

The yeast vector to be constructed is assembled from three (or more) component parts. Minimally these parts consist of 1) a yeast selectable marker (11), 2) a yeast DNA replication element (14), and 3) a gene to be cloned (17). Methods to construct vectors suitable for yeast transformation from these component parts are described.

FIG. 1, DNA fragment (11)—A DNA fragment containing a yeast selectable marker. Typically this fragment will serve as a template for amplification by PCR (using DNA primers 10 and 12) from a yeast vector containing the selectable marker. Alternately, a linear fragment containing the selectable marker could be used as a template.

FIG. 1, DNA fragment (14)—A DNA fragment containing a yeast DNA origin of replication (ARS—autonomously replicating sequence) element. Optionally this fragment can contain, in addition to the DNA replication origin, a stability element such as a centromere or a 2μ STAB sequence. Typically this fragment will serve as a template for amplification by PCR (using DNA primers 13 and 15) from a yeast vector containing a yeast replication origin (and optionally a stability element). Alternately, a linear fragment containing an ARS and optionally a STAB element could be used as a template.

FIG. 1, DNA fragment (17)—A DNA fragment containing the gene to be cloned. Typically this fragment will serve as a template for amplification by PCR (using DNA primers 16 and 18) from a cloning vector containing the gene. Alternately, a linear fragment containing the gene could be used as a template.

FIG. 1, DNA primer (10). Primer homologous to one end of the top strand of the yeast marker gene (11), to be used in combination with primer (12) to amplify the DNA substrate (11) using the PCR process FIG. 1, DNA primer (12). Primer with a 3' end homologous to the other end of the bottom strand of the yeast marker gene (11) and with a 5' end complementary to primer (13).

FIG. 1, DNA primer (13). Primer homologous to one end of the top strand of the yeast replication sequence element (14), to be used in combination with primer (15) to amplify the DNA substrate (14) using the PCR process.

FIG. 1, DNA primer (15). Primer with a 3' end homologous to the other end of the bottom strand of the yeast replication element (14) and with a 5' end complementary to primer (16).

FIG. 1, DNA primer (16). Primer homologous to one end of the top strand of the gene to be cloned (17).

FIG. 1, DNA primer (18). Primer with a 3' end complementary to the other end of the top strand of the gene to be cloned (17) and with a 5' end complementary to primer (10).

Primer (12) and primer (10) are used in the PCR process to amplify a linear DNA using the yeast marker gene (11) as a substrate. The fragment generated (20) bears the yeast selectable marker and an end homologous to the fragment (22) that bears the yeast replication element, introduced as a result of the PCR process using the primer (12).

Primer (13) and primer (15) are used in the PCR process to amplify a linear DNA using the yeast DNA replication element (14) as a substrate. The fragment generated (22) bears the yeast replication element and an end homologous to the fragment (24) that bears the gene to be cloned, introduced as a result of the PCR process using the primer (15).

Primer (16) and primer (18) are used in the PCR process to amplify a linear DNA using the gene to be cloned (17) as a substrate. The fragment generated (24) bears the gene to be cloned and an end homologous to the fragment (20) that bears the yeast selectable marker, introduced as a result of the PCR process using the primer (18).

DNA fragments (20), (22), and (24) are mixed an used to transform the yeast *S. cerevisiae* using standard procedures. The transformants are subjected to the appropriate selection for the selectable marker carried on the DNA element (11).

FIG. 1, (26). Recombination intermediate that occurs in vivo.

FIG. 1, (28). Following recombination, a circular plasmid results from the in vivo recombination process.

The transformed yeast can be examined directly for phenotypes that might be associated with the cloned gene, for example a growth phenotype or a visual enzymatic activity.

DNA can be isolated from individual colonies (or from cultures derived from individual colonies) to verify the plasmid construction and/or to test in other ways (for example, to transfer the plasmid into a new yeast strain for subsequent analysis).

Figure 2:
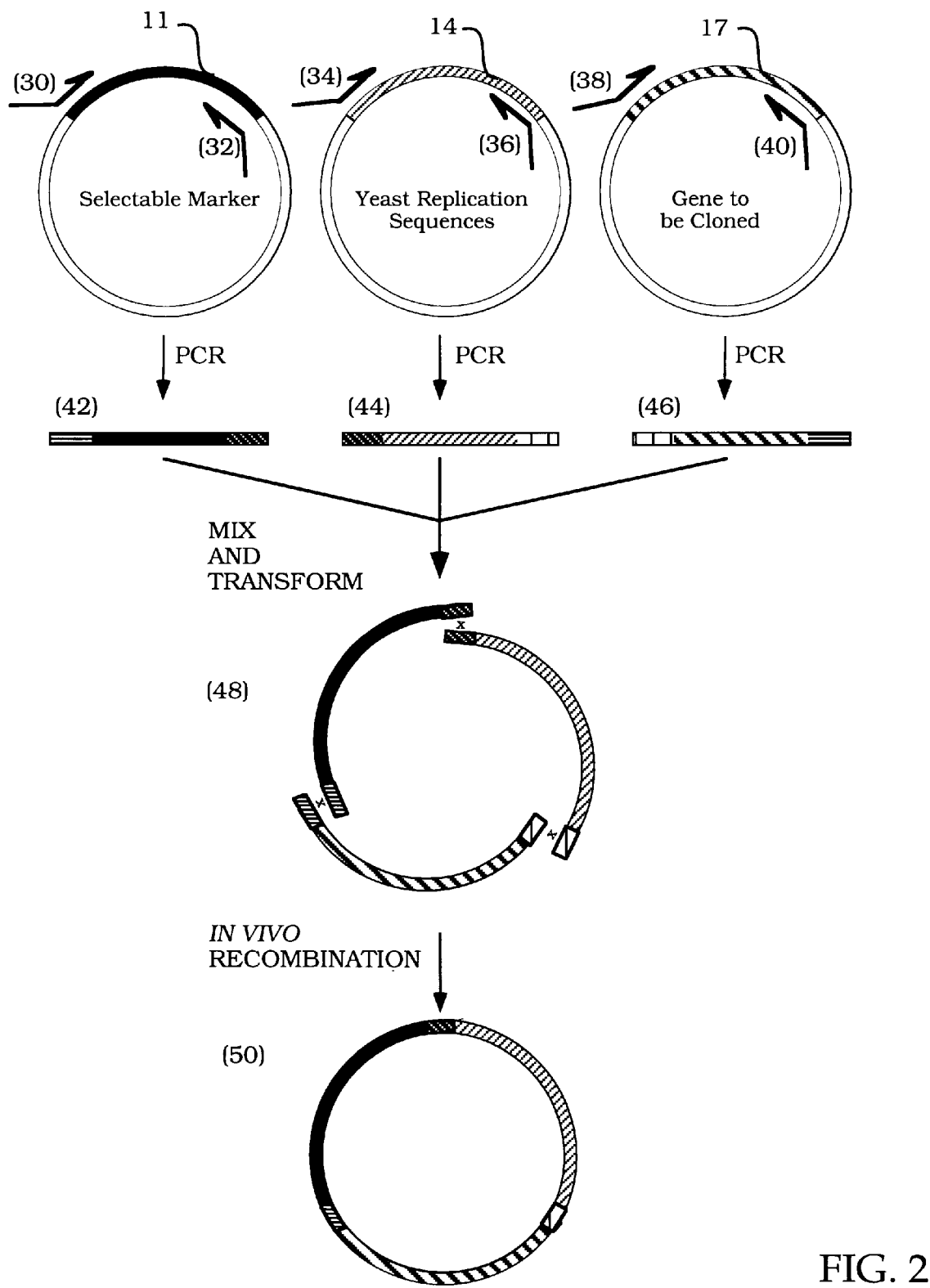

FIG. 2 A Multifragment Cloning Method Based on Homology Introduced at Both Ends of Each Fragment in a Series Another method of cloning DNA is described. This method is based on the ability to create a series of overlapping DNA fragments by introducing at one end of each DNA fragment a sequence element homologous to one added to the previous DNA fragment in the series, and by introducing at the other end of each DNA fragment a different sequence element also added to the next DNA fragment in the series (see FIG. 2).

This method can be used to construct vectors that contain specific sequence information separating the other DNA elements of the plasmid (as in FIG. 2, between the selectable marker, the yeast replication sequence, and the gene to be cloned). For example, by designing the primer (30) and the primer (40) so that their 5' portions are complementary and each contain the same restriction enzyme recognition sequence, a specific site can be introduced between the selectable marker and the gene to be cloned. Likewise, the primer pairs (32 and 34) and (36 and 38) can be designed to each introduce (via their complementary 5' ends) a unique DNA sequence separating the plasmid parts that they join.

This method requires a host with an efficient and highly accurate recombination system. We have found the yeast S. cerevisiae serves as a suitable transformation host for this method. We have tested many strains of S. cerevisiae and all have served as suitable hosts. We have tested other possible transformation hosts, including several strains of E. coli, but have not identified any other hosts suitable for use in this method.

The yeast vector to be constructed is assembled (see FIG. 2) from three (or more) component parts. Minimally these parts consist of 1) a yeast selectable marker (11), 2) a yeast DNA replication element (14), and 3) a yeast gene to be cloned (17). Methods to construct vectors suitable for yeast transformation from these component parts are described.

FIG. 2, DNA fragment (11)—A DNA fragment containing a yeast selectable marker. Typically this fragment will serve as a template for amplification by PCR (using DNA primers 30 and 32) from a yeast vector containing the selectable marker. Alternately, a linear fragment containing the selectable marker could be used as a template.

FIG. 2, DNA fragment (14)—A DNA fragment containing a yeast DNA origin of replication (ARS—autonomously replicating sequence) element. Optionally this fragment can contain, in addition to the DNA replication origin, a stability element such as a centromere or a $2\mu$ STAB sequence. Typically this fragment will serve as a template for amplification by PCR (using DNA primers 34 and 36) from a yeast vector containing a yeast replication origin (and optionally a stability element). Alternately, a linear fragment containing an ARS and optionally a STAB element could be used as a template.

FIG. 2, DNA fragment (17)—A DNA fragment containing the gene to be cloned. Typically this fragment will serve as a template for amplification by PCR (using DNA primers 38 and 40) from a cloning vector containing the gene. Alternately, a linear fragment containing the gene could be used as a template.

FIG. 2, DNA primer (30)—A primer with a 3' end homologous to one end of the top strand of the yeast marker gene (11) and with a 5' end complementary to the 5' end of primer (40), to be used in conjunction with DNA primer (32) to amplify DNA containing the selectable marker (11) to generate fragment (42)

FIG. 2, DNA primer (32). Primer with a 3' end homologous to the other end of the bottom strand of the yeast marker gene (11) and with a 5' end complementary to the 5' end of primer (34).

FIG. 2, DNA primer (34). Primer with a 3' end homologous to one end of the top strand of a yeast replication sequence element (14) and with a 5' end complementary to the 5' end of primer (32).

FIG. 2, DNA primer (36). Primer with a 3' end homologous to the other end of the bottom strand of the yeast replication element (14) and with a 5' end complementary to the 5' end of primer (38).

FIG. 2, DNA primer (38). Primer with a 3' end homologous to one end of the top strand of the gene to be cloned (17) and with a 5' end complementary to the 5' end of primer (36).

FIG. 2, DNA primer (40). Primer with a 3' end homologous to the top strand of the gene to be cloned (17) and with a 5' end complementary to the 5' end of primer (30).

FIG. 2, DNA fragment (42). DNA fragment generated using the PCR process bearing the yeast selectable marker and a 5' end (a synthetic recombination target) derived from the 5' end of the primer (30) as well as a 3' end (a second synthetic recombination target) derived from the 5' end of the primer (32)

FIG. 2, DNA fragment (44). DNA fragment generated using the PCR process bearing the yeast replication element and a 5' end (a synthetic recombination target) derived from the 5' end of the primer (34) as well as a 3' end (a second synthetic recombination target) derived from the 5' end of the primer (36)

FIG. 2, DNA fragment (46). DNA fragment generated using the PCR process bearing the gene to be cloned and a 5' end (a synthetic recombination target) derived from the 5' end of the primer (38) as well as a 3' end (a second synthetic recombination target) derived from the 5' end of the primer (40).

DNA fragments (42), (44), and (46) are mixed and used to transform the yeast S. cerevisiae using standard procedures. The transformants are subjected to the appropriate selection for the selectable marker carried on the DNA element (11).

FIG. 2, (48). Recombination intermediate that occurs in vivo.

FIG. 2, (50) Following recombination, a circular plasmid results from the in vivo recombination process, bearing the yeast selectable marker (11), the yeast replication sequence (14), and the gene to be cloned (17). The yeast selectable marker (11) and the yeast replication sequence (14) recombine at the synthetic recombination targets found at the 3' end of the DNA fragment (42) and the 5' end of the DNA fragment (44) and thus are linked. The yeast replication sequence (14) and the gene to be cloned (17) recombine at the synthetic recombination targets found at the 3' end of the DNA fragment (44) and the 5' end of the DNA fragment (46) and thus are linked. The gene to be cloned (17) and the yeast selectable marker (11) recombine at the synthetic recombination targets found at the 3' end of the DNA fragment (46) and the 5' end of the DNA fragment (42) and thus are linked. These three recombination events together can create a circular plasmid that contains a DNA replication sequence (14) (ARS) as well as a yeast selectable marker (11) and the gene to be cloned (17). Thus, selection for the yeast marker (and concomitantly the DNA replication origin (14)) selects for plasmids that have undergone the "3-way recombination" and so contain the gene to be cloned.

The transformed yeast that bear recombinant circular plasmids that include the DNA for the selectable marker (11) grow to form colonies on a yeast transformation plate of the appropriate nutritional selection. For example, when using the HIS3 gene to complement a his3⁻ mutation, one would select for the proper yeast on plates lacking histidine.

These transformed yeast can be examined directly for phenotypes that might be associated with the cloned gene, for example a growth phenotype or a visual enzymatic activity.

DNA can be isolated from individual colonies (or from cultures derived from single colonies) to verify the plasmid construction and/or to test in other ways (for example, to transfer the plasmid into a new yeast strain for subsequent analysis).

Figure 3:
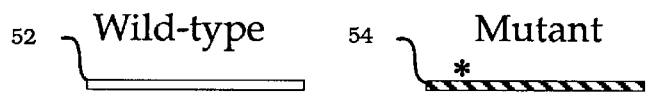
Figure 3:
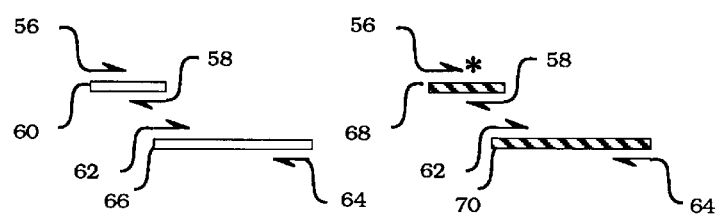
Figure 3:
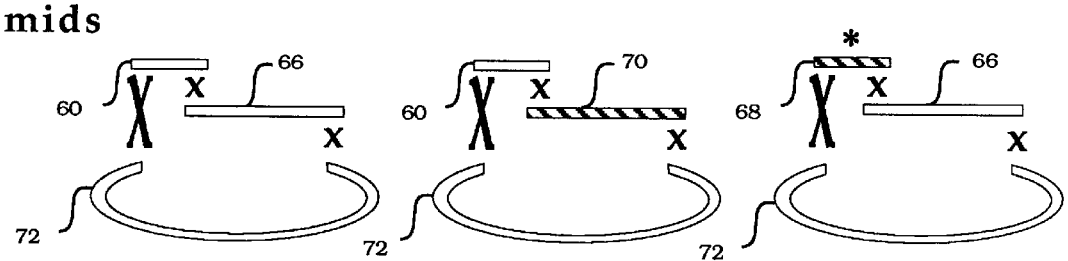

FIG. 3 A Method of Recombinational Mapping of Mutations
Mapping mutations using multifragment in vivo cloning.

A method is presented for mapping the location of a mutation within a gene phenotypically expressed in yeast. We have developed this method to rapidly map mutations that disrupt an interaction identified using the two-hybrid system originally described by Fields, S. & Song, O.-k. (Nature 340: 245–246, 1989). This method can be used to map the location of mutations within genes that are expressed in yeast so long as the gene function can be identified by some phenotypic assay. Thus genes from yeast or other organisms can be studied if they are associated with a phenotype such as growth (ie. a nutritional requirement, or complementation of an essential function), an assayable enzymatic activity, or an interaction that is coupled to such an identifiable phenotype.

Wild-type and mutant genes would typically be contained on plasmids that replicate and express in yeast, but might also be from plasmids that do not replicate in yeast, or from linear DNA fragments. These plasmids (or linear fragments derived from them), are shown in FIG. 3. A wild-type gene (52), and a mutant gene (54) (the asterisk indicates the location of a mutation that will be mapped in an example) serve as substrates for PCR using the primer pairs (56 and 58) and (62 and 64). Primers (58) and (62) are designed so that either they overlap, or so that they amplify fragments which overlap. We have found that an overlap with as few as 17 nucleotides is sufficient.

In a first container, primer (56) and primer (58) (see FIG. 3) are used to amplify by PCR the left side of the WT gene (52) to generate DNA fragment (60). It is important to use a polymerase with low error rates such as Pfu DNA polymerase, so that a minimal number of errors are introduced that might otherwise obscure the mapping data.

In a second container, primer (62) and primer (64) (see FIG. 3) are used to amplify by PCR the right side of the WT gene (52) to generate DNA fragment (66). It is important to use a polymerase with low error rates such as Pfu DNA polymerase, so that a minimal number of errors are introduced that might otherwise obscure the mapping data.

In a third container, primer (56) and primer (58) (see FIG. 3) are used to amplify by PCR the left side of the mutant gene (54) to generate DNA fragment (68). It is important to use a polymerase with low error rates such as Pfu DNA polymerase, so that a minimal number of errors are introduced that might otherwise obscure the mapping data.

In a fourth container, primer (62) and primer (64) (see FIG. 3) are used to amplify by PCR the right side of the mutant gene (54) to generate DNA fragment (70). It is important to use a polymerase with low error rates such as Pfu DNA polymerase, so that a minimal number of errors are introduced that might otherwise obscure the mapping data.

Primers (58) and (62) (see FIG. 3) are designed so that the 3' end of the left fragment (60) and the 5' end of the right fragment (66) contain a region of overlap, or homology. (In FIG. 3, the DNA fragment pairs (68) and (70), (60) and (70) and finally (68) and (66) have the same overlap as the pair (60) and (66). We have used overlaps as small as 17 bp.

In a fifth container, a gapped acceptor vector (72) is generated by cutting a plasmid (that can replicate and be selected for in yeast) with a suitable restriction enzyme. A linearized (gapped) plasmid is unable to replicate in yeast. The gapped plasmid (72) contains homology (near one end of the gap) with the 5' end of the left fragment (60) and also contains homology (near the other end of the gap) with the 3' end of the right fragment (66). Alternately, a linearized plasmid with the same structure can be generated using PCR; however, due to the size of many of the yeast plasmids used to construct gapped acceptor vectors, the PCR reaction is often inefficient.

In a sixth container, an aliquot of DNA fragment (60) amplified by the PCR reaction from container 1 is mixed with an aliquot of DNA fragment (66) amplified by the PCR reaction from container 2. To this mixture is added gapped acceptor plasmid (72) from container 5. This mixture is used to transform yeast by standard techniques, selecting for the marker present on the gapped acceptor plasmid. The gapped acceptor plasmid and the left and right fragments undergo a "3-way" recombination to generate a circular plasmid (see FIG. 3). The circular plasmid generated will replicate and can be selected for in yeast using standard methods. This transformation represents a wild-type reconstruction.

In a seventh container, an aliquot of DNA fragment (60) amplified by the PCR reaction from container 1 is mixed with an aliquot of DNA fragment (70) amplified by the PCR reaction from container 4. To this mixture is added gapped acceptor plasmid (72) from container 5. This mixture is used to transform yeast by standard techniques, selecting for the marker present on the gapped acceptor plasmid. The gapped acceptor plasmid and the left and right fragments undergo a "3-way" recombination to generate a circular plasmid. The circular plasmid generated will replicate and can be selected for in yeast using standard methods. This transformation tests the location of the mutation; it will regenerate a phenotypically wild-type plasmid if the mutation had been in fragment (68) (as diagramed in FIG. 3), and a phenotypically mutant plasmid if the mutation had been in fragment (70).

In an eighth container, an aliquot of DNA fragment (68) amplified by the PCR reaction from container 3 is mixed with an aliquot of DNA fragment (66) amplified by the PCR reaction from container 2. To this mixture is added gapped acceptor plasmid (72) from container 5. This mixture is used to transform yeast by standard techniques, selecting for the marker present on the gapped acceptor plasmid. The gapped acceptor plasmid (72) and the left (68) and right (66) fragments undergo a "3-way" recombination to generate a circular plasmid. The circular plasmid generated will replicate and can be selected for in yeast using standard methods. This transformation tests the location of the mutation; it will regenerate a phenotypically wild-type plasmid if the mutation had been in the right fragment (70), and a phenotypically mutant plasmid if the mutation had been in the left fragment (68) (as diagramed in FIG. 3).

Figure 5:
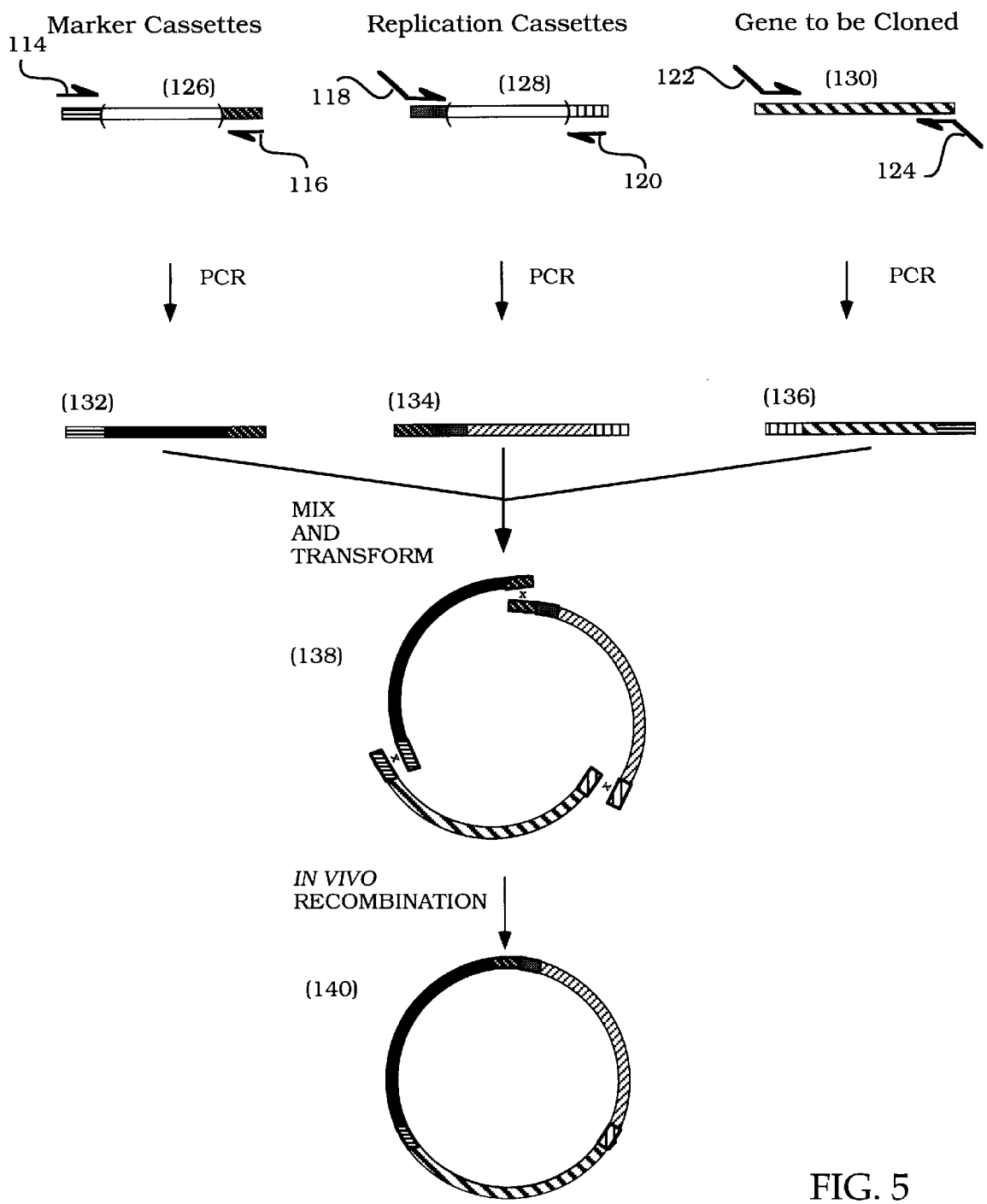

FIG. 5 Cassette-Based Cloning Methods

A method to construct plasmids in yeast from overlapping DNA cassettes using multifragment in vivo recombination.

Sources of yeast marker gene(s), yeast DNA replication sequences(s), and a gene to be cloned are constructed by standard cloning techniques, or obtained by other means.

A source of the marker gene (126) (see FIG. 5) with a sequence element homologous to the primer (114) and with another sequence element complementary to the primer sequence (116) surrounding a gene that can be selected for in yeast (a yeast marker). These sequence elements can serve both as priming sites for PCR amplification and as recombination targets in subsequent steps. In one preferred embodiment, a series of different (yeast marker) fragments are constructed, each with a different selectable marker, but surrounded by the same PCR priming sites/recombination targets. For example, this can be achieved by cloning a series of yeast marker genes into a common plasmid at a defined location on the plasmid, for example into a polylinker. These cassettes serve as interchangeable sources of a yeast marker gene in subsequent recombination steps.

Source of the replication cassette (128) (see FIG. 5) with a sequence element homologous to the 3' end of primer (118) and another sequence element complementary to the primer sequence (120) surrounding a yeast DNA replication origin (or ARS for Autonomously Replicating Sequence) and optionally a centromere or other stability sequence such as the 2μ STAB element. These sequence elements can serve as priming sites for PCR amplification. The sequence element complementary to the primer sequence (120) can serve as a recombination target in subsequent steps. In one preferred embodiment, a series of different (DNA replication) fragments are constructed, each with a different yeast DNA replication origin and/or stability element flanked by the same PCR priming sites. For example, this can be achieved by cloning a series of DNA replication elements into a common plasmid at a defined location on the plasmid, for example into a polylinker. These cassettes serve as interchangeable sources of a yeast replication element in subsequent recombination steps.

A source of the gene to be cloned (130) (see FIG. 5). This source could be a plasmid containing the gene, a linear fragment containing the gene, genomic DNA containing the gene, or a cDNA mixture containing the gene.

One method to construct the linear DNA fragment (132) with a recombination element homologous to the primer (114) and another recombination element complementary to the primer sequence (116):

Primer (114) (see FIG. 5) is homologous to the 5' end of the top strand of (126) which serves as a source of the yeast selectable marker gene. Primer (116) is complementary to the 3' end of the top strand of (126). Primers (114) and (116) are then used as primers in a PCR amplification using DNA fragment (126) as a substrate to amplify DNA fragment (132).

One method to construct the linear DNA fragment (134) with a recombination element complementary to the primer (116) and another recombination element complementary to the primer sequence (120): Primer (118) (FIG. 5) was designed such that the 5' end is complementary to primer (116) and the 3' end of primer (118) is homologous to the sequence at the 5' end of the top strand of the yeast replication cassette (128). Primer (120) (FIG. 5) is complementary to the sequence at the 3' end of the top strand of the yeast replication cassette (128). Primers (118) and (120) are then used as primers in a PCR amplification using the replication cassette (128) as a substrate (either from a plasmid with this sequence element, or from a linear fragment with this element) to generate the linear fragment (134).

One method to construct the linear DNA fragment (136) with a recombination element complementary to the primer (114) and another recombination element complementary to the primer sequence (120):

Primer (122) (FIG. 5) was designed such that the 5' end of primer (122) is complementary to primer (120) and the 3' end of primer (122) is homologous to the sequence at the 5' end of the top strand of the gene to be cloned on DNA element (130). Primer (124) (FIG. 5) was designed so that the 5' end of primer (124) is complementary to primer (114) and the 3' end of primer (124) is complementary to the 3' end of the top strand of the gene to be cloned on DNA element (130). Primers (122) and (124) are then used as primers in a PCR amplification using the source (for example, a plasmid of a linear fragment) of the gene to be cloned (130), as a substrate to generate DNA fragment (136).

The recombination targets [the sequence element homologous to primer (114), the sequence element complementary to primer (116), and the sequence element complementary to primer (120)] can be synthetic sequences (not derived from functional yeast sequences) designed solely as recombination targets. Alternately, these recombination sequences [the sequence element homologous to primer (114), the sequence element complementary to primer (116), and the sequence element complementary to primer (120)] could be functional elements such as promoter (UAS) or terminator elements. Or, alternately, these recombination sequences [the sequence element homologous to primer (114), the sequence element complementary to primer (116), and the sequence element complementary to primer (120)] might be designed to introduce restriction sites or other specific DNA sequences that might be useful in conventional cloning or DNA amplifications.

DNA Fragments (132), (134), and (136) are mixed and used to transform yeast, selecting for the marker on DNA fragment (132).

These fragments recombine in yeast, represented by the in vivo recombination intermediate (138) (see FIG. 5). The sequence element complementary to primer (116) at one end of DNA fragment (132) recombines with the sequence element complementary to primer (116) at one end of DNA fragment (134). The sequence element complementary to primer (120) at one end of DNA fragment (134) recombines with the sequence element complementary to primer (120) at one end of DNA fragment (136). The sequence element homologous to primer (114) at one end of DNA fragment (136) recombines with the sequence element homologous to primer (114) at one end of DNA fragment (132).

These three recombination events join together the three overlapping DNA fragments (132), (134), and (136) into a circular plasmid (140) that contains a DNA replication sequence (128), a yeast selectable marker (126), and the gene to be cloned (130). Any circular plasmids formed that do not contain both the DNA replication sequences (a yeast ARS element) and the yeast selectable marker gene will not be replicated and maintained during selection for the yeast marker. The homologous recombination process in yeast is highly efficient and the majority of the plasmids that survive the transformation and selection process are found to have incorporated the other fragment (fragments 136 this example) that were designed to create a circular DNA plasmid molecule upon recombination in vivo.

The transformed yeast cells that bear recombinant circular plasmids grow to form colonies on a yeast transformation plate that selects for the yeast marker derived from DNA fragment (132).

Isolates of plasmid DNA with the correct structure can be identified and isolated by preparing DNA from several single yeast colonies (or cultures derived from single colonies) and examining this DNA directly (by restriction enzyme analysis or PCR analysis) to confirm that the plasmid construction was successful. This DNA can be used to transform *E. coli* in order to generate large quantities of plasmid DNA.

The transformed yeast can be examined directly for phenotypes that might be caused by the cloned gene; for example a growth phenotype.

One possible modification of this method would be the construction of marker cassettes and replication cassettes that contain telomeres at the ends. In this case the selection would not be the formation of a circular plasmid that was able to replicate, but rather the formation of a linear plasmid that could replicate in yeast. In this case one would join a telomere+marker cassette and a telomere+replication cassette via an intermediate DNA fragment containing at one end a region homologous to the telomere-distal end of the telomere+marker cassette and at the other end a region homologous to the telomere distal end of the telomere+ replication cassette.

Figure 6C:
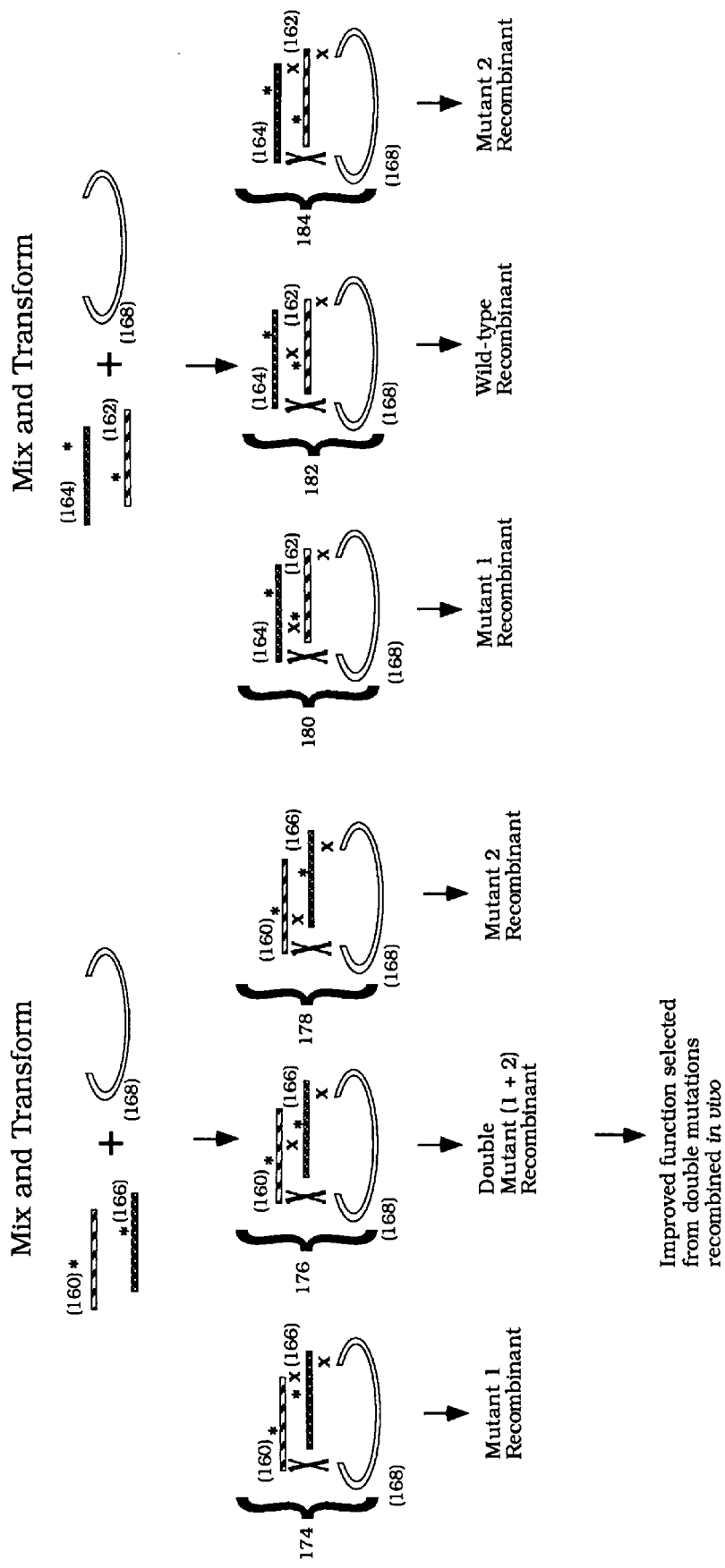

FIG. 6. Directed-Evolution Based on Multifragment Cloning

A method of accelerated in vivo evolution (mutagenesis in vitro, followed by sexual in vivo recombination that results in the reassortment of multiple mutations, followed by genetic selection for advantageous combinations of the multiple mutations).

A method is described to generate and identify combinations of multiple mutations that alter a function (specificity, activity, affinity, etc.) of an enzyme (or other protein or DNA or RNA molecule). In particular, multifragment cloning in vivo provides a means of recombining multiple mutations (that are each alone responsible for a small functional change) into compositie multimutants (exhibiting a composite phenotype), thus allowing the efficient creation of new macromolecules with significantly modified function.

An "evolution cassette" (141) (FIG. 6), including the gene to be mutated, is mutagenized using standard techniques, or by mutagenic PCR.

The "evolution cassette" (141) (FIG. 6) includes regions that flank the gene to be mutated and that are homologous with the ends of the gapped recipient vector (168). Primer (142) is homologous to the 5' end of the top strand of the evolution cassette (141). Primer (148) is complementary to the 3' end of the top strand of the evolution cassette (141). Primer (146) is homologous to the 5' end of the top strand of the region of the "evolution cassette" containing the region of the gene to be mutagenized and evolved. Primers (142) and (146) should not have any overlap (or homology). Primer (144) is complementary to the 3' end of the top strand of the region of the "evolution cassette" containing the region of the gene to be mutagenized and evolved. Primers (144) and (148) should not have any overlap (or homology).

The "evolution cassette" (141) may be mutagenized using standard techniques. Then a pool of linear mutagenized "evolution cassette" DNA fragments is generated by PCR amplification of the mutagenized "evolution cassette" DNA using primer (142) and primer (148) and a thermostable DNA polymerase with a low error rate such as Pfu DNA polymerase.

Alternatively, the "evolution cassette" may be mutagenized and amplified in one step by mutagenic PCR. A pool of mutagenized "evolution cassette" DNA fragments is generated by PCR amplification of wild-type DNA (141) using primer (142) and primer (148) and an error prone thermostable DNA polymerase such as Taq DNA polymerase.

The gapped yeast plasmid (168) is derived from a yeast plasmid that can replicate and be selected for in yeast. This plasmid can be generated either by linearizing a plasmid with an appropriate restriction enzyme (or pair of enzymes) or by using the PCR process to amplify the region of the plasmid. Such a plasmid contains a yeast replication sequence (ARS-autonomously replicating sequence) and a yeast marker gene that can be selected in yeast following transformation (such as a nutritional marker).

In addition, this vector contains a recombination sequence element that is also present at the 5' end of the "evolution cassette" DNA fragment (the 5' recombination sequence) and a recombination sequence element that is also present at the 3' end of the "evolution cassette" DNA fragment (the 3' recombination sequence). The polarity of the 5' and 3' recombination sequence elements is the same as in the "evolution cassette".

The pool of mutagenized "evolution cassette" DNA (generated by either of the above two procedures) is mixed with the gapped recipient vector (168) and used to transform yeast using standard techniques, selecting for the yeast marker present on the gapped plasmid. The gapped acceptor plasmid and the mutagenized "evolution cassette" undergo recombination in vivo to generate a circular plasmid. The circular plasmid generated will replicate and can be selected for in yeast using standard methods. Yeast containing plasmids which have incorporated the "evolution cassette" DNA will grow into colonies on transformation plates when selection is maintained for the yeast marker present on the gapped plasmid.

Yeast bearing mutant plasmids can be identified by an appropriate screen or selection for the desired mutations. Yeast bearing plasmids with mutations conferring upon the "gene to be mutated" (an enzyme or other protein, DNA or RNA molecule) an intermediate (or small) change in specificity and/or activity and/or affinity are thus identified.

Yeast bearing mutant plasmids with the desired mutations are pooled and their plasmid DNA is isolated to be used in the following steps of in vivo recombination.

In one container, DNA is amplified using the pool of mutant plasmid DNAs as a substrate for a PCR reaction using primers (142) and (144), thus generating a pool of mutant DNA fragments with a recombination target sequence 5' of the gene to be mutated. DNA fragment (160) is such a fragment derived from one particular mutation present in this pool of mutated DNA. DNA fragment (164) is another such a fragment derived from a different mutant DNA present in this pool of mutated DNA. DNA fragment (156) is another such a fragment derived from a wild-type DNA present in this pool of mutated DNA.

In a second container, DNA is amplified using the pool of mutant plasmid DNAs as a substrate for a PCR reaction using primers (146) and (148), thus generating a pool of mutant DNA fragments with a recombination target sequence 3' of the gene to be mutated. DNA fragment (162) is such a DNA fragment derived from one particular mutation present in this pool of mutated DNA. DNA fragment (166) is another such a fragment derived from a different mutant DNA present in this pool of mutated DNA. DNA fragment (158) is another such a fragment derived from a wild-type DNA present in this pool of mutated DNA.

The pool of "5' recombination sequence+gene to be mutated" DNA (similar to the wild-type fragment (156), only this is a pool of various mutant DNAs) and the pool of "gene to be mutated+ 3' recombination sequence" DNA (similar to the wild-type fragment (158), only this is a pool of various mutant DNAs) are mixed with the gapped recipient vector and used to transform yeast using standard techniques, selecting for the yeast marker present on the gapped plasmid. The gapped acceptor plasmid, the "5' recombination sequence+gene to be mutated" DNA, and the "gene to be mutated+ 3' recombination sequence" DNA undergo a 3-way recombination in vivo to generate a circular plasmid. Recombination intermediate (170) represents the recombination between the gapped vector (168) and the two wild-type DNA fragments (156) and (158), regenerating a wild-type copy of the gene on a plasmid. Recombination intermediate (172) represents the recombination between the gapped vector (168) and the mutant 1 DNA fragments (160) and (162), regenerating a mutant copy of the gene (bearing mutation 1) on a plasmid. Recombination intermediate (186) represents the recombination between the gapped vector (168) and the mutant 2 DNA fragments (164) and (166), regenerating a mutant copy of the gene (bearing mutation 2) on a plasmid.

Intermediates (174), (176), (178), (180), (182), and (184) represent the many different recombination intermediates that can be formed between the mutant 1 DNA fragment (160) and the mutant 2 DNA fragment (166) or between the mutant 2 DNA fragment (162) and the mutant 1 DNA fragment (164).

Recombination intermediates (174) and (180) regenerate a mutation 1-bearing DNA.

Recombination intermediate (182) regenerates a wild-type DNA.

Recombination intermediates (178) and (184) regenerate a mutation 2-bearing DNA.

Recombination intermediate (176) is of particular interest, because it represents the class of recombinants that have successfully recombined two mutant DNAs into one DNA bearing both mutations.

The circular plasmids generated will replicate and can be selected for in yeast using standard methods. Yeast containing plasmids with the mutated gene of interest will grow into colonies on transformation plates when selection is maintained for the yeast marker present on the gapped plasmid.

Among the double mutants represented by the recombination intermediate (176), one expects to find double mutants that have an improved function. Such evolved genes can be identified using a suitable phenotypic screen or selection.

This process of recombination and selection can be repeated multiple times, allowing for a combinatorial search of multiple mutants by recombining and screening pools of preselected mutants, thus avoiding the impossibly large task of separately creating and testing all possible combinations of multiple mutations.

Yeast bearing mutant plasmids are identified, and plasmid DNA is isolated from individuals to obtain the evolved genes.

The present invention can be illustrated by the following non-limiting example.

Mapping by Multifragment Cloning in vivo

An efficient method for mapping mutations is described in which hybrid genes, derived partly from mutant and partly from wild-type DNA, are obtained in vivo by homologous recombination of multiple fragments. The recombinants are formed in a strain in which their phenotypes are immediately apparent. This method was developed to identify changes that disrupt protein-protein interactions demonstrable by the two-hybrid system in yeast. However, it can be extended to any system where recombination is possible, provided an assay is available to distinguish between mutant and wild-type phenotypes.

Traditional cloning methods are often inefficient (Sambrook, J., Fritsch, E. F. & Maniatis, T. (1989) *Molecular Cloning* (Cold Spring Harbor Laboratory Press, Cold Spring Harbor)). They commonly involve several in vitro steps of DNA manipulation. Finding the desired end product requires arduous screening of this DNA after it has been transformed into a suitable host, usually *Escherichia coli*. Nevertheless, many aspects of molecular genetics rely heavily upon such methods.

Take, for example, the generation and cloning of random but localized mutations (Shortle, D., DiMaio, D. & Nathans, D. (1981) *Annu. Rev. Genetics* 15, 265–294). Such an undertaking usually begins with mutagenesis, either chemical or otherwise, of the target DNA sequence. The target might be one specific gene, which in *E. coli* would be 1 kb in length, on average. Often, a plasmid-borne copy of this gene is the target of mutagenesis. Mutations generated in this way have already been cloned, but could include changes in the cloning vector as well as in the gene of interest. Alternatively, the target to be mutagenized might be a piece of DNA containing this gene and nothing else. To be useful, mutations generated in this way must still be cloned and identified.

It is not always possible to rig a mutagenic treatment to generate the preferred frequency of mutational events. Too low a mutation rate increases the amount of work required to find changes of interest. Too high a mutation rate requires that one distinguish which of multiple base changes are responsible for the mutant phenotype. In any event, the importance of specific base changes must be verified. Traditional methods for doing this involve physically separating multiple changes, given the availability of useful restriction sites, or reconstructing each mutant separately by one of any number of protocols for site-directed mutagenesis (Herlitze, S. & Koenen, M. (1990) *Gene* 91, 143–147; Kunkel, T. A. (1985) *Proc. Natl. Acad. Sci. USA* 82, 488–492.; Zoller, M. J. & Smith, M. (1987) *Methods Enzymol.* 154, 329–350.–5), all of which require at least one primer per specific mutation.

In a separate report, we will describe our use of the two-hybrid system (Chien, C.-t., Bartel, P. L., Sternglanz, R. & Fields, S. (1991) *Proc. Natl. Acad. Sci. USA* 88, 9578–9582.; Fields, S. & Song, O.-k. (1989) *Nature* (London) 340, 245–246) to identify a strong interaction between two components of the flagellar motor of *E. coli*, FliG and FliM, and our mutational analysis of this interaction (D. L. Marykwas and H. C. Berg, manuscript in preparation). Here we describe a facile method for mapping the location of mutations within genes. We illustrate this method by application to interaction-defective mutations in fliG.

MATERIALS AND METHODS

Strains and Plasmids. *S. cerevisiae* strain GGY1::171 (Gill, G. & Ptashne, M. (1987) *Cell* 51, 121–126) was used for two-hybrid screening (Chien, C.-t., Bartel, P. L., Sternglanz, R. & Fields, S. (1991) *Proc. Natl. Acad. Sci. USA* 88, 9578–9582). *E. coli* strain DH5α (from Bethesda Research Laboratories) was used for most traditional cloning. Plasmid pBD-G$^{WT}$ encoded the GAL4 DNA-binding domain fusion to wild-type (WT) FliG. Plasmid pAD-M$^{WT}$ encoded the GAL4 activation domain fusion to WT FliM. The construction of these plasmids will be described elsewhere (D. L. Marykwas and H. C. Berg, manuscript in preparation), as will be the isolation of fliG mutant derivatives of plasmid pBD-G$^{WT}$, named pBD-G$^{10}$, pBD-G$^{15}$, and pBD-G$^{25}$, to represent mutants 10, 15, and 25, respectively. Plasmid pMA424 is the GAL4 DNA-binding domain cloning vector described by Ma and Ptashne (Ma, J. & Ptashne, M. (1987) *Cell* 51, 113–119).

DNA Amplification. PCR primers (Table 1) were supplied by Integrated DNA Technologies. Modified Pfu polymerase was from BioInsight. A typical amplification reaction was performed in a total volume of 100 μl containing 0.02 to 2 ng of template plasmid DNA, 25 nmoles of each dNTP, 20 pmoles of each primer, and 4 units of polymerase in the buffer recommended by the enzyme manufacturer. The magnesium concentration often had to be optimized, the final concentration usually ranging between 2 and 10 mM. Reactions were performed in a MiniCycler from MJ Research as follows: 94° C. for 5 min; 25 cycles of 94° C. for 45 s, 50° C. for 1.5 min, 72° C. for 1.5 min; 72° C. for 5 min. Sometimes the annealing temperature was different than 50° C., determined either by the melting temperature of the primers involved or empirically. Reaction products were examined for yield and purity by gel electrophoresis and cleaned up over QIAquick columns (from QIAGEN) prior to use. Removal of reaction buffer, nucleotides and primers was not necessary for in vivo mapping, but was required if the reaction products were to be sequenced.

Yeast Transformations. Yeast cells were grown on complete synthetic dropout medium (CSM-deleted component) containing per liter: 6.7 g yeast nitrogen base without amino acids, Difco; 1× drop-out supplement mixture (defining the deleted component), BIO101; and 20 g glucose. Yeast cells were transformed following the single-stranded carrier method of Gietz and Schiestl (Gietz, R. D. & Schiestl, R. H. (1991) Yeast 7, 253–263). CSM-his lacks histidine, allowing the selection of His+ transformants. CSM-leu lacks leucine, allowing the selection of Leu+ transformants. CSM-his-leu lacks both histidine and leucine, allowing double selection. In a given mapping experiment, GGY1::171 yeast cells already harboring pAD-M$^{WT}$ were cotransformed with 5 $\mu$l of each PCR product (10 to 75 ng each) and 1 $\mu$l (33 to 100 ng) of linear gapped pMA424 (prepared by restriction enzyme digestion with both EcoRI and BamHI, followed by phenol extraction and ethanol precipitation). The resident plasmid pAD-M$^{WT}$ contained the selectable LEU2 gene. The recombinant plasmid constructed in vivo, derived from pMA424, contained the HIS3 gene. Therefore, transformants containing both plasmids were selected at 30° C. on CSM-his-leu plates.

Two-hybrid Screening. Yeast transformants were scored for their interaction phenotype on SSX-his-leu plates (CSM-his-leu plates with 0.1 M KH$_2$ $_{PO4}$, pH 7.0, 0.05% [wt/vol] 5-bromo-4-chloro-3-indolyl $\beta$-D-galactoside [X-gal], and sucrose in place of glucose). The transformants were directly lifted onto Millipore HA filters and placed colony-side-up onto the SSX-his-leu plates, which were then incubated at 30° C. Color was scored after 1 or 2 days. Usually whole plates were tested, each representing the in vivo recombination of one mutant gene segment with the remaining WT gene segment. The reciprocal experiment was then tested on a separate SSX-his-leu plate. Sometimes side-by-side comparison of reciprocal experiments were performed on the same plate by lifting colonies onto smaller Millipore HA filters (25 instead of 85 mm dia.), several of which easily fit on a plate. However, fewer independent recombinants could be sampled in this way.

Plasmid Rescue. Plasmid DNA was extracted from yeast cells by the method of Ward (Ward, A. C. (1990) Nucleic Acids Res. 18, 5319). The plasmids to be recovered that contained the subcloned fliG alleles all carried the HIS3 gene; therefore, cells containing these recombinant subclones were grown under His+ selection. One $\mu$l of the extracted DNA was then transformed into E. coli strain DH5$\alpha$, made electrocompetent as described by Dower et al. (Dower, W. J., Miller, J. F. & Ragsdale, C. W. (1988) Nucleic Acids Res. 16, 6127–6145); ampicillin-resistant colonies were selected. Although grown under His+ selection and not Leu+ selection, the yeast cells might also have harbored the LEU2-containing plasmid pAD-M$^{WT}$. Plasmids isolated from E. coli transformed with either HIS3-containing plasmid DNA (the recombinant) or LEU2-containing plasmid DNA were easy to distinguish electrophoretically, because the plasmids were of different size and had different restriction patterns.

DNA Sequence Analysis. Plasmid DNA was sequenced following the double-stranded plasmid sequencing protocol of Del Sal et al. (Del Sal, G., Manfioletti, G. & Schneider, C. (1989) Biotechniques 7, 514–519), except that we used Sequenase, [$^{33}$P$\alpha$]dATP, and as template ¹⁄₁₀th of the DNA obtained from a 1.5 ml boiling miniprep. PCR products were sequenced using the procedure described by Thein (Thein, S. L. (1989) Comments 16, 8), with [$^{33}$P$\alpha$]dATP.

RESULTS

The Method, in Principle. Our mapping method takes advantage of the highly efficient recombination system found in S. cerevisiae (Muhlrad, D., Hunter, R. & Parker, R. (1992) Yeast 8, 79–82.; Rothstein, R. (1991) Methods Enzymol. 194, 281–301). We have found that yeast can repair plasmid gaps using not only one homologous fragment, but multiple fragments with overlapping homology. This feature has allowed us to construct hybrid genes in vivo, derived partly from the mutant and partly from the WT, unrestricted by the availability of convenient restriction sites.

The DNAs used for the development of this method express two components of the flagellar motor of E. coli that interact, FliG and FliM (D. L. Marykwas and H. C. Berg, manuscript in preparation). When FliG fused to the DNA-binding domain of GAL4 and FliM fused to a transcriptional activation domain of GAL4 were coexpressed in yeast, they reconstituted a functional GAL4-like transcription factor that activated the expression of a GAL4-dependent lacZ reporter gene. We also generated a collection of plasmid-borne FliG mutants (fused to the DNA-binding domain) that interact with FliM less well than does WT FliG (D. L. Marykwas and H. C. Berg, manuscript in preparation). To identify the fliG mutations responsible for the reduced FliG/FliM interaction, we developed the method described here and illustrated in FIG. 3.

We have made chimeras of mutant and WT fliG genes (fused in frame with DNA encoding GAL4's DNA-binding domain). We generated the parts via PCR using modified Pfu polymerase, which performs more faithful proofreading than does Taq polymerase. The parts were designed to overlap to provide homology. The non-overlapping ends have homology with the cloning vector (in this case the DNA-binding domain vector). All three pieces together, without ligase, are transformed into yeast and undergo in vivo recombination. The activation domain fusion to FliM, and the reporter gene, are already present, allowing direct screening of the blue phenotype.

FIG. 3 shows that when both parts are derived from the WT fliG fusion, in vivo recombination with the binding domain vector results in cells that are dark blue, the WT phenotype, indicating a positive FliG/FliM interaction. In the example illustrated, when the left part is derived from WT and the right part is from the mutant, in vivo recombination also results in a WT dark blue phenotype. However, in the converse experiment, when the left part is derived from the fliG mutant and the right part is from WT, the result is light blue, the mutant phenotype. Therefore, in the example shown, the fliG mutation responsible for reducing the FliG/FliM interaction maps to the left part of the mutant gene. If any fliG mutations are present in the right half of the fliG mutant, they are silent in this assay and therefore not responsible for the reduced FliG/FliM interaction.

Figure 4:
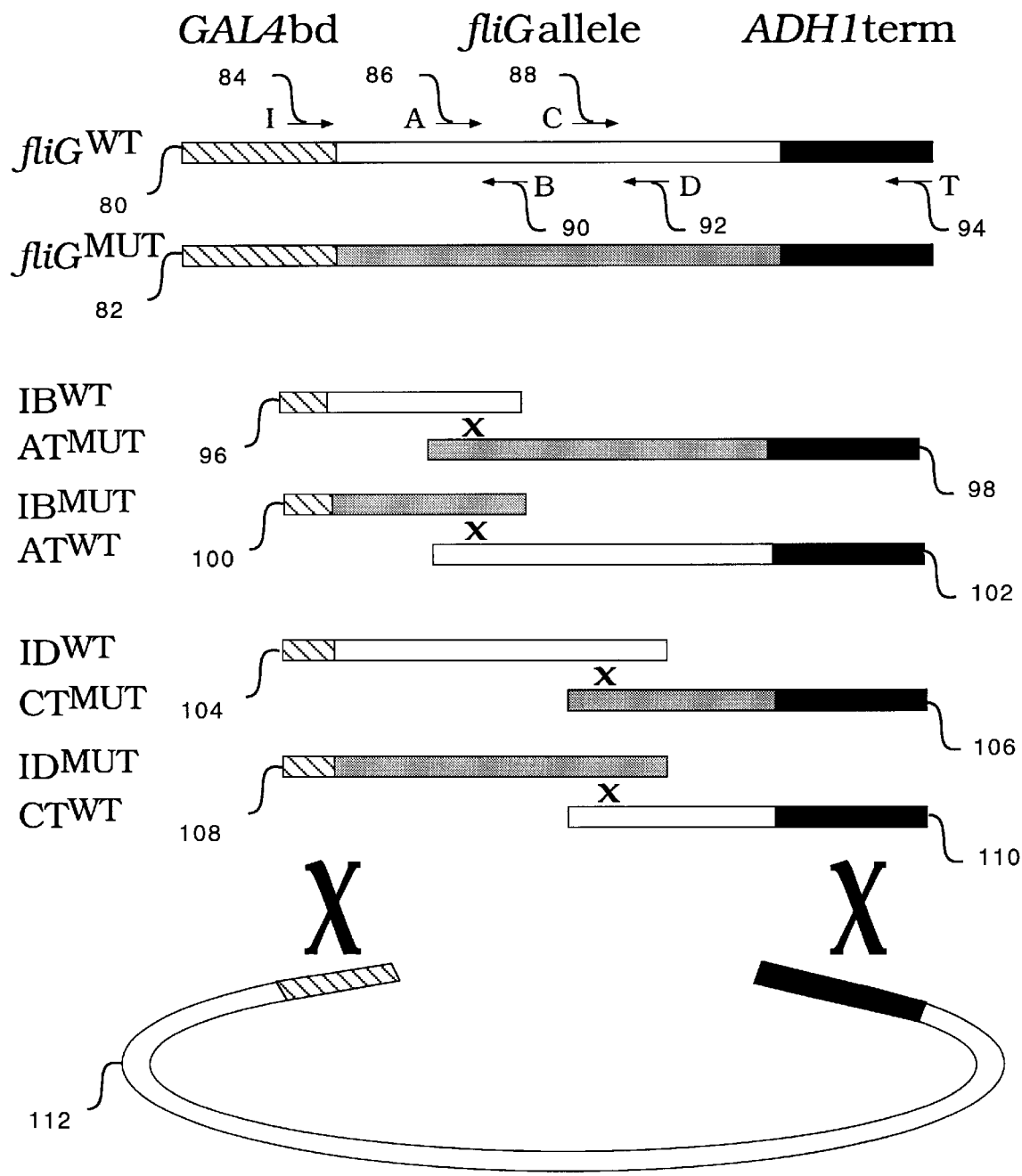

Strategy to Map ftiG Mutants. We isolated 18 interaction-defective fliG mutants (D. L. Marykwas and H. C. Berg, manuscript in preparation). Our strategy to map these mutations is illustrated in FIG. 4. The fliG coding region is 996 bp in length, including the stop codon. Primer oGAL132-137 primes within GAL4 sequences upstream of the fliG coding sequence in our clones (pBD-G$^{WT}$, pBD-G$^{10}$, pBD-G$^{15}$, and pBD-G$^{25}$). oADHterm primes within the ADH1 transcriptional terminator located downstream of the fliG coding sequence in our clones. Primers mapoGa, mapoGb, mapoGc, and mapoGd prime within the fliG coding sequence. These primers were used to amplify various parts of fliG. PCR with primers oGAL132-137 and mapoGb gave fragment IB, containing the first third of fliG. PCR with primers mapoGa and oADHterm gave fragment AT, containing the remaining two-thirds of fliG. Primers mapoGa and mapoGb prime on opposite strands of fliG, providing fragments IB and AT with a region of overlap 107 bp in length. Similarly, fragment ID, containing the first two-thirds of fliG, was generated with primers oGAL132-137 and mapoGd, whereas fragment CT, containing the remaining third of fliG, was generated with primers mapoGc and oADHterm, with a region of overlap 99 bp in length. The non-overlapping ends of each pair of overlapping fragments share homology (52 bp and 192 bp) with pMA424 (the vector for the DNA-binding domain).

For each fliG mutant to be mapped, hybrids were generated by the in vivo recombination (with linear gapped pMA424) of mutant IB with WT AT, and compared to the reciprocal recombination of mutant AT with WT IB. Another pair of reciprocal hybrids were generated combining WT and mutant ID and CT fragments. The information obtained from these four combinations was enough to determine whether the fliG change responsible for the interaction-defective mutant phenotype laid within the first, second, or third portion of the fliG gene. In effect, we have divided the fliG gene into three regions of similar size, the ends of which were defined by the PCR primers used to generate the mapping fragments.

A Simple Case. Table 2 shows mapping data for three representative fliG mutants. One of these was mutant 25. The mutation responsible for the interaction-defective phenotype of this mutant did not map to segment IB$^{25}$ (IB amplified from pAD-G$^{25}$ as template), containing the first third of the mutant fliG gene, nor to CT$^{25}$, containing the last third of the mutant fliG gene. Instead, the responsible change mapped to segments AT$^{25}$ and ID$^{25}$. The in vivo recombinants generated with either of these mutant segments were light blue (the mutant phenotype) when tested for the FliG/FliM two-hybrid interaction on X-gal plates.

These two segments have in common the middle third of the mutant fliG gene. Indeed, DNA sequencing of mutant 25 has revealed a single base change in this region. It results in a his155→pro substitution (sequence data not shown).

A More Complicated Example. fliG mutant 15 clearly mapped to segment AT$^{15}$, not to segment IB$^{15}$ (Table 2). However, in vivo recombination using segments ID and CT led to a mixed population of both mutant and WT recombinants, in about equal ratio, whether the mutant fragment was ID$^{15}$ or CT$^{15}$. This mutation did not map clearly to either one of these fragments. Instead, the mapping data suggest that fliG mutant 15 maps to the region of overlap between fragments ID and CT. Indeed, DNA sequencing of mutant 15 has revealed a single base change in this region spanning the 99 bp overlap. It results in a leu225→pro substitution (sequence data not shown).

Separating Two Closely Linked Base Changes. fliG mutant 10 also mapped to the middle third of the mutant gene (Table 2). However, DNA sequencing revealed two closely linked single base changes in the mutant gene (not shown), separated by only 35 bp. As each change resulted in an amino acid substitution (gln141→arg; leu153→pro), we were not able to determine, a priori, which of the two changes was responsible for the mutant phenotype. To distinguish the two possibilities, we generated hybrids that contained one or the other but not both of these changes. The forward primer mapoGI and the reverse primer mapoGn recognize the sequence that separates the two base changes but prime on opposite strands of the gene. PCR with primers oGAL132-137 and mapoGn gave fragment IN, whereas PCR with mapoGI and oADHterm gave fragment LT, with an overlap 33 bp in length. In vivo recombination using IN$^{10}$ and LT$^{WT}$ gave recombinants that appeared WT for the FliG/FliM interaction, whereas LT$^{10}$/IN$^{WT}$ recombinants exhibited the mutant phenotype (Table 3). This determined that the L153P substitution was responsible for the interaction-defective phenotype of fliG mutant 10; the Q141R substitution was phenotypically silent in this assay. As expected, the in vivo recombination of vector and mutant fragment LD$^{10}$ with WT fragments IN$^{WT}$ and CT$^{WT}$ (4 pieces total) also yielded mutant recombinants (Table 3). Plasmid DNA isolated from these cells was sequenced and found to contain the expected single base change.

DISCUSSION

We have described a new way to map mutations in DNA by multifragment in vivo cloning. We have illustrated this method by mapping fliG mutations that disrupt the FliG/FliM two-hybrid interaction. Hybrids of mutant and WT fliG genes were created in yeast in vivo by homologous recombination and scored directly for their interaction phenotypes. Since yeast cells are transformed under conditions of no growth, each recombinant provided an independent test of the location of the mutation being mapped. For example, the 479 light blue ID$^{25}$/CT$^{WT}$ recombinants (Table 2) represent 479 separate tests showing that mutation 25 mapped to segment ID. If traditional cloning methods had been used, comparable data could have been obtained only by constructing 479 independent subclones in vitro, testing these 479 subclones in vivo by transforming them separately into yeast, and then scoring their phenotypes.

Mutations can be mapped by multifragment in vivo cloning to a high degree of resolution. We chose to determine if our fliG mutants mapped to the first, second, or last third of the 996 bp fliG gene and designed primers accordingly. We felt that a 300 bp map segment was small enough to sequence efficiently. However, one can divide a gene into as many map segments as desired, limited only by the number of primers used. One of the mapped mutations described (mutant 15) was localized to a small 99 bp region. This was possible due to its fortuitous map location in the homologous region of overlap between two mapping segments. Therefore, the smallest region to which a mutation can be mapped (in one experiment) is limited by the smallest amount of homology required for overlapping map segments to recombine in vivo. We have not yet defined the lowest limit of overlap necessary for recombination; however, a 33 bp overlap is sufficient.

Occasionally, a mutation might be covered by one of the mapping primers. Indeed, this has been the case with some of our fliG mutants (unpublished data). These still map to the region of overlap between the map segments involved. However, we have found that modified Pfu polymerase does not always repair primer mismatches as little as 1 bp removed from the annealed 3' end. Therefore, if a WT primer covers a mutation, that primer will usually be extended, yielding a PCR product that is WT for the covered mutation.

An alternative method for recombinational mapping of plasmid-borne genes in yeast has already been described (Kunes, S., Ma, H., Overbye, K., Fox, M. S. & Botstein, D. (1987) *Genetics* 115, 73–81). It involves testing the ability of an individual restriction fragment to correct a plasmid-borne mutation by gene conversion. Our method of multifragment in vivo cloning differs from that of Kunes et al. in many ways. We use multiple overlapping fragments, not just one fragment, to close a plasmid gap in vivo. In this way, we construct plasmid subclones that acquire the mutation of interest from a specific DNA fragment, with success rates of nearly 100%. By contrast, the method of Kunes et al. relies upon the incidence of loss of a plasmid-borne mutation to identify its location; in the end, the mutation is lost, not subcloned. Our method, the construction and testing of reciprocal hybrids in vivo, provides redundant information that should identify both where the responsible change is and where it is not. Kunes' method fails to do so. This is another important difference. A mutant gene might contain multiple base changes; each could have a mutant phenotype or they could act together to create one. This information can be reconstructed using our method but would be lost with theirs. Alternatively, all but one mutation might be silent and located in regions sequenced outside of the identified map location. Such silent mutations might reveal the extent to which certain parts of a gene may be altered without affecting the specific gene function being assayed. Indeed, we have found several fliG mutations that do not significantly affect the FliG/FliM two-hybrid interaction (D. L. Marykwas and H. C. Berg, manuscript in preparation). Identification of such regions should prove informative, but would not have been possible had we used the method of Kunes et al.

Multifragment in vivo cloning relies heavily upon the use of PCR and therefore shares many of the same pitfalls. Since our primary use is for mapping mutations, we reduce the likelihood of creating additional mutations by using a thermophilic enzyme that does not introduce errors too frequently. Based on our cumulative sequencing of cloned PCR products, we have found <1 base change for every 10 kb of modified Pfu-amplified DNA, compared to 1 base change for every 280 bp amplified by Taq polymerase under the conditions we use. Nevertheless, although modified Pfu polymerase proofreads, errors are still made and sometimes visible in our mapping data. Mapping by multifragment in vivo cloning is sensitive to the presence of starting template in the PCR-derived mapping fragments. Our starting templates are plasmids encoding mutant or WT FliG fused to the GAL4 DNA-binding domain. Any template molecules transformed into yeast will provide a background of transformants that exhibit the template-dependent phenotype. To avoid excessive template-related background problems, we use very little starting template, or we perform two consecutive amplifications, using the reaction products of the first amplification as the template for the second. Obviously, multifragment in vivo cloning could also give ambiguous results if the template was a mixed population of mutant and WT plasmids. Finally, not every pair of overlapping fragments gives equivalent transformation frequencies, we believe when either fragment is limiting due to poor amplification via some primer pairs.

There are some problems associated with multifragment in vivo cloning that are unrelated to PCR. We always have a background of tan yeast transformants that do not display reporter gene activity on indicator plates (see Tables 2 and 3). Based on control transformations, we attribute these to incompletely cut vector and to illegitimate recombination of the vector; we have observed both. We have also seen variable efficiencies of in vivo recombination, even when the same DNA was used, but on different days with different cell cultures. This variability appeared to be due to differences in yeast cell competence, as transformation with intact plasmid appeared to change in the same way.

There have been several recent reports of in vivo cloning in E. coli (Jones, D. H. & Howard, B. H. (1990) Biotechniques 8, 178–183; Jones, D. H. & Howard, B. H. (1991) Biotechniques 10, 62–66; Jones, D. H. & Winistorfer, S. C. (1992) Biotechniques 12, 528–535; Oliner, J. D., Kinzler, K. W. & Vogelstein, B. (1993) Nucleic Acids Res). None of these methods have been applied to the mapping of mutations. Nor have any involved the recombination of more than two DNA fragments. Our mapping is routinely done with three pieces (the vector plus two overlapping inserts) and has also worked quite well with four (see Table 3). The recent reports all cite a requirement for absolute homology at the free ends of the vector being recombined. Although homology is also required for our in vivo recombination of multiple fragments in yeast, the homology is not strictly necessary at either end of our gapped vector or insert and may be internal at each end. Ends with as few as 2 and as many as 327 non-homologous base pairs work just as well as ends with absolute homology (our unpublished observations).

Finally, our multifragment in vivo cloning is much more efficient than any of the published procedures, even those described to work in Rec+ strains of E. coli. We transformed yeast with linear vector DNA and a full length fliG-containing piece with homology to the cloning vector at both of its ends. Using the same DNA, we transformed two different recombination-proficient strains of E. coli, including a recD strain reported to allow efficient uptake and recombination of linear DNA. We also compared the transformation of yeast versus E. coli with three overlapping pieces, as in most of our mapping experiments. We were unable to detect recombination products of three DNA fragments in E. coli. We obtained a single recombinant of two pieces from E. coli, but many thousands from the same DNA transformed into S. cerevisiae (data not shown).

In conclusion, multifragment in vivo cloning provides an easy way to map mutations. It facilitates the physical separation of multiple changes in a target sequence. The converse should also be true. It should simplify the joining of multiple base changes into one composite multi-mutant, as might be required to perform accelerated in vivo evolution experiments. As we will report in a separate article, the same principles we use to map and subclone mutations can be applied to constructing complex custom-made plasmids by the in vivo recombination of DNA cassettes designed to overlap. Therefore, multifragment in vivo cloning provides a new approach towards genetic manipulation that should eliminate steps requiring bacterial hosts and the foreign DNA sequence elements necessary for replication and selection in these hosts. Thus, beer and wine makers and other workers in the agricultural industry might genetically engineer a better product in a manner that is commercially acceptable. Multifragment in vivo cloning is a powerful mapping tool, especially when combined with the two-hybrid system. However, it should be possible to use this method in any transformable organism where efficient homologous recombination is possible and where mutants and non-mutants are distinguishable.

FIG. 3. Mapping mutations using in vivo recombination. The WT gene is represented by open rectangles, the mutant gene by the filled rectangles. The mutation to be mapped is indicated by an asterisk. PCR primers are shown as arrows. One pair of primers is used to amplify the left part of each gene. A second pair of primers is used to amplify the right part. The gene parts overlap with each other and with a cloning vector, shown by the ovals. The regions of overlap allow homologous recombination as indicated by an X.

Hybrids are created in vivo by the recombination of mutant and WT fragments, and then scored directly for their phenotype. Pairs of reciprocal hybrids are tested, for comparison. Both WT fragments are also recombined, as a positive control. In the example shown, the mutation is in the left fragment of the mutant gene.

FIG. 4. Strategy used to map fliG mutants. The top bar represents the gene organization of fliG in pBD-G$^{WT}$. The next bar represents a fliG mutant derived from this plasmid. GAL4 bd encodes the GAL4 DNA-binding domain. ADH1 term is a transcription termination sequence from the yeast ADH1 gene. The arrows represent the relative positions of PCR primers (described in Table 1) used to amplify various parts of fliG: I=oGAL132-137, T=oADHterm, A=mapoGa, B=mapoGb, C=mapoGc, and D=mapoGd. Regions of overlap that allow homologous recombination in vivo are each indicated by an X. The pairs of gene fragments that are recombined in vivo are shown. Each fragment is defined (and labeled) by the primers used for its amplification. Hybrids of mutant and WT fliG are created by recombining one mutant fragment with one WT fragment. Pairs of reciprocal hybrids are always tested, for comparison.

TABLE 1

Primers used in this study

| Name | Sequence | Priming site |
|---|---|---|
| oGAL132-137 | 5'- tcatcggaagagagtagt -3' | 394 → 411 |
| oADHterm | 5'- gagcgacctcatgctatacc -3' | 1213 → 1194 |
| mapoGa | 5'- agatattctcgaaactcg -3' | 285 → 302 |
| mapoGb | 5'- cgataatttgcggatgct -3' | 391 → 374 |
| mapoGc | 5'- ctgatgaaaactcagcag -3' | 613 → 630 |
| mapoGd | 5'- ctcgaacaggaacatctc -3' | 711 → 694 |
| mapoGl | 5'- gccgccgatattctggcgt -3' | 424 → 442 |
| mapoGn | 5'- acgttcatcgaacaac -3' | 456 → 441 |

The priming site relative to +1 of the respective structural gene: GAL4 for oGAL132-137, ADH1 for oADHterm, and fliG for mapoGa–mapoGn.

TABLE 2

Representative mapping data

| Mutant fragment | fliG mutant number | | |
|---|---|---|---|
| | 10 | 15 | 25 |
| IB | 30 DB (100%) | 111 DB (97.4%) | 34 DB (100%) |
| | 15 tan | 3 LB (2.6%) | 26 tan |
| | | 100 tan | |
| AT | 15 LB (100%) | 9 LB (100%) | 18 LB (100%) |
| | 16 tan | 77 tan | 30 tan |
| ID | 225 tan | 184 DB (51%) | 8 M/DB (1.6%) |
| | | 175 LB (48.5%) | 479 LB (98.4%) |
| | | 2 MB (0.5%) | 122 tan |
| | | 67 tan | |
| CT | 263 DB (98.5%) | 200 DB (51.5%) | 107 DB (97.3%) |
| | 4 LB (1.5%) | 188 LB (48.5%) | 3 MB (2.7%) |
| | 96 tan | 112 tan | 111 tan | fliG mutants 10, 15, and 25 were mapped by in vivo recombination as described in the text. Mutant IB fragments were recombined with AT$^{WT}$. Mutant AT fragments were recombined with IB$^{WT}$. Mutant ID fragments were recombined with CT$^{WT}$. Mutant CT fragments were recombined with ID$^{WT}$. For each pair of mutant and WT fragments so joined, the total number of transformants displaying each phenotype is given, followed in parentheses by that same number expressed as the percentage of total recombinants. LB is light blue. MB is medium blue. DB is dark blue. Tan transformants are not considered to be recombinants (see Discussion). The in vivo recombination of ID$^{10}$ with CT$^{WT}$ never gave anything but tan transformants. More definitive fliG mutant 10 mapping data is shown in Table 3.

TABLE 3

More fliG mutant 10 mapping data

| Fragments combined in vivo | Recombinant phenotypes | | |
|---|---|---|---|
| IN$^{WT}$ + LT$^{10}$ | 0 DB | 23 LB (100%) | 115 tan |
| IN$^{10}$ + LT$^{WT}$ | 68 DB (97%) | 2 LB (3%) | 96 tan |
| IN$^{WT}$ + LD$^{WT}$ + CT$^{WT}$ | 103 DB (100%) | 0 LB | 500 tan |
| IN$^{10}$ + LD$^{10}$ + CT$^{10}$ | 7 DB (2.6%) | 260 LB (97.4%) | 550 tan |
| IN$^{10}$ + LD$^{WT}$ + CT$^{WT}$ | 700 DB (99.4%) | 4 M/LB (0.6%) | 520 tan |
| IN$^{WT}$ + LD$^{10}$ + CT$^{WT}$ | 2 DB (5%) | 38 LB (95%) | 560 tan |
| IN$^{WT}$ + LD$^{WT}$ + CT$^{10}$ | 241 DB (97.6%) | 6 LB (2.4%) | 506 tan |

Mapping fragments were amplified from either WT or mutant 10 template DNA. Each mapping fragment is named after the primers and template used for its amplification. For example, IN$^{WT}$ fragments were amplified from WT template using primers oGAL132-137 (I) and mapoGn (N). Likewise, LT$^{10}$ fragments were amplified from mutant 10 template using primers mapoGl (L) and oADHterm (T). Other primers used were mapoGc (C) and mapoGd (D).

Conclusion, Ramifications, and Scope

In particular, the present invention relates to a general method for cloning that can be practiced using any organism with a suitably efficient and precise in vivo recombination system.

This method can be used to construct plasmids that are composed entirely of DNA isolated from the host organism, provided suitable DNA replication and selectable markers are available for use in that organism.

This method can serve as the basis for a cassette-based cloning system, where suitably designed plasmids serve as sources for 1) linear fragments containing DNA replication elements flanked by specific DNA sequence elements that serve as recombination tags, and 2) linear fragments containing selectable markers flanked by specific DNA sequence elements that serve as recombination tags. Thus plasmid constructions can be greatly simplified by the use of such a cassette-based cloning system.

The present invention also relates to a method of mapping mutations. This is both a rapid and simple method for mapping mutations. We have used this method to map the position of mutations that disrupted a two-hybrid interaction between the E. coli proteins FliG and FliM.

Additionally, the invention relates to a method of recombination that can be used to reassort mutations in vivo and thus can facilitate directed-evolution by multiple iterations of a procedure that selects for and then reasserts mutations.

Although the descriptions above contain many specificities, these should not be construed as limiting the scope of the invention but as merely providing some of the presently preferred embodiments of this invention.

Thus, the scope of the invention should be determined by the appended claims and their legal equivalents, rather than by the examples given.

What is claimed is:

1. A method for synthesizing a double-stranded circular DNA molecule, the method comprising the steps of:
   (i) in a first container means, amplifying from a first double-stranded circular DNA molecule a first double-stranded DNA segment by means of a polymerase chain reaction (PCR) process, wherein a plurality of primers are provided so that two primers effect the amplification and one primer adds a nucleotide sequence to the first segment, the sequence being homologous to a second double-stranded DNA segment to which the first segment is to be joined;
   (ii) in a second container means, amplifying from a second double-stranded circular DNA molecule a second double-stranded DNA segment by means of the PCR process, wherein a plurality of primers are provided so that two primers effect the amplification and one primer adds a nucleotide sequence to the second segment, the sequence being homologous to a third double-stranded DNA segment to which the second segment is to be joined;
   (iii) in a third container means amplifying from a third double-stranded circular DNA molecule a third double-stranded DNA segment by means of the PCR process, wherein a plurality of primers are provided so that two primers effect the amplification and one primer adds a nucleotide sequence to the third segment, the sequence being homologous to the first double-stranded DNA segment to which the third segment is to be joined;
   (iv) transforming the product of step (i), and the product of step (ii), and the product of step (iii) together into a host with a suitable, efficient, and accurate in vivo recombination system; and
   (v) allowing the product of step (ii) to recombine in vivo at the homologous sequence added to the product of step (i), allowing the product of step (iii) to recombine at the homologous sequence added to the product of step (ii), and allowing the product of step (i) to recombine at the homologous sequence added to the product of step (iii), thereby producing a fourth double-stranded circular DNA molecule.

2. The method of claim 1 wherein the host is yeast.

3. The method of claim 1 wherein at least one homologous sequence added to one double-stranded DNA segment in steps (i), (ii) and (iii) is located at one end of the DNA segment.

4. The method of claim 1 wherein at least one homologous sequence added to one double-stranded DNA segment in steps (i), (ii) and (iii) is located between two opposing ends of the DNA segment.

5. The method of claim 1 wherein
   (i) the first double-stranded DNA segment contains in vivo selection means; and (ii) the second double-stranded DNA segment contains in vivo DNA replication means, so as to provide the doubled-stranded circular DNA molecule produced in step (v) in vivo selection means, and in vivo DNA replication means.

6. The method of claim 1 wherein prior to the step of transforming in step (iv), at least one additional double-stranded DNA segment is amplified from at least one additional double-stranded DNA molecule by means of the PCR process to include at one end a nucleotide sequence that is homologous to a sequence in a DNA segment to which said at least one additional DNA segment is to be joined, such that said at least one additional double-stranded DNA segment is subsequently transformed into the host in step (iv) and recombined in step (v) along with the products of steps (i), (ii), and (iii).

7. The method of claim 6 wherein said at least one additional DNA segment further includes a homologous sequence at an end opposite the one end.

8. A method for synthesizing a double-stranded circular DNA molecule, the method comprising the steps of:
(i) in a first container means, amplifying from a first double-stranded DNA molecule a first double-stranded DNA segment by means of a polymerase chain reaction (PCR) process, wherein a plurality of primers are provided so that two primers effect the amplification, the first segment having a nucleotide sequence that is homologous to a sequence in a second double-stranded DNA segment to which the first segment is to be joined;
(ii) in a second container means, amplifying from a second double-stranded DNA molecule the second double-stranded DNA segment by means of the PCR process, wherein a plurality of primers are provided so that two primers effect the amplification, the second segment having a nucleotide sequence that is homologous to a sequence in a third double-stranded DNA segment to which the second segment is to be joined;
(iii) in a third container means, amplifying from a third double-stranded DNA molecule the third double-stranded DNA segment by means of the PCR process, wherein a plurality of primers are provided so that two primers effect the amplification, the third segment having a nucleotide sequence that is homologous to a sequence in the first double-stranded DNA segment to which the third segment is to be joined;
wherein the first, second, and third double-stranded DNA molecules are different from one another and at least one of the first, second, and third double-stranded DNA molecules is linear;

(iv) transforming the product of step (i), and the product of step (ii), and the product of step (iii) together into a host with a suitable, efficient, and accurate in vivo recombination system; and
(v) allowing the product of step (ii) to recombine in vivo at the homologous sequence added to the product of step (i), allowing the product of step (iii) to recombine at the homologous sequence added to the product of step (ii), and allowing the product of step (i) to recombine at the homologous sequence added to the product of step (iii), thereby producing a double-stranded circular DNA molecule.

9. The method of claim 6 wherein at least one of said at least one additional double-stranded DNA molecule is a linear DNA molecule.

10. The method of claim 6 wherein at least one of said at least one additional double-stranded DNA molecule is a circular DNA molecule.

11. The method of claim 3 wherein the step of amplifying in steps (i), (ii) and (iii) further includes adding a homologous sequence to an opposite end of the DNA segment by means of a primer different from the primer adding the nucleotide sequence to the one end of the DNA segment.

12. The method of claim 8 wherein the homologous sequence in each double-stranded DNA segment in steps (i), (ii) and (iii) is located at one end of the DNA segment.

13. The method of claim 12 wherein the step of amplifying in steps (i), (ii) and (iii) further includes adding a homologous sequence to an opposite end of the DNA segment by means of a primer different from the primer adding the nucleotide sequence to the one end of the DNA segment.

14. The method of claim 8 wherein the homologous sequence in each double-stranded DNA segment in steps (i), (ii) and (iii) is located between two opposing ends of the DNA segment.

15. The method of claim 8 wherein prior to the step of transforming in step (v), at least one additional double-stranded DNA segment is amplified from at least one additional DNA molecule by means of the PCR process to include a nucleotide sequence that is homologous to a sequence in a DNA segment to which said at least one additional DNA segment is to be joined, such that said at least one additional double-stranded DNA segment is subsequently transformed into the host in step (iv) and recombine in step (v) along with the products of steps (i), (ii), and (iii).

* * * * *